US006518315B1

(12) United States Patent
Roufogalis et al.

(10) Patent No.: US 6,518,315 B1
(45) Date of Patent: Feb. 11, 2003

(54) MEDICINAL USES OF PHENYLAIKANOLS AND DERIVATIVES

(75) Inventors: Basil Don Roufogalis, Pymble; Colin Charles Duke, Randwick; Van Hoan Tran, Bankstown, all of (AU)

(73) Assignee: The University of Sydney (AU)

( * ) Notice: Subject to any disclaimer, the term of this patent is extended or adjusted under 35 U.S.C. 154(b) by 0 days.

(21) Appl. No.: 09/509,829

(22) PCT Filed: Oct. 20, 1998

(86) PCT No.: PCT/AU98/00870

§ 371 (c)(1), (2), (4) Date: Jun. 23, 2000

(87) PCT Pub. No.: WO99/20589

PCT Pub. Date: Apr. 29, 1999

(30) Foreign Application Priority Data

Oct. 21, 1997 (AT) ............................................ 9900/97

(51) Int. Cl.[7] ............................................ A01N 35/00

(52) U.S. Cl. ........................ 514/678; 568/716; 568/764; 549/434; 435/156

(58) Field of Search ................................ 568/716, 764; 435/156; 549/434, 445; 514/678

(56) References Cited

FOREIGN PATENT DOCUMENTS

| | | |
|---|---|---|
| EP | 516082 | 12/1992 |
| JP | 61-134338 | 6/1986 |
| JP | 63-072625 | 4/1988 |
| JP | 1-066138 | 3/1989 |
| JP | 1-216923 | 8/1989 |
| JP | 4-202127 | 7/1992 |
| JP | 4-202128 | 7/1992 |
| JP | 8-040970 | 2/1996 |
| WO | 9215543 | 9/1992 |

OTHER PUBLICATIONS

Aeschbach, R., Loliger, J., Scott, B.C., Murcia, A., Butler, J., Halliwell, B. and Aruoma, O.I. Antioxidant actions of thymol, carvacrol, 6–gingerol, zingerone and hydroxytyrosol. Food and Chemical Toxicology (1994), 32, 31–36.

Antiplatelet Trialists' Collaboration. Collaborative overview of randomised trials of antiplatelet therapy–I: Prevention of death, myocardial infarction, and stroke by prolonged antiplatelet therapy in various categories of patients. BMJ (1994), 308, 81–106.

Belan, A., Bolte, J., Fauve, A., Gourcy, J.G. and Veschambre, H. Use of biological systems for the preparation of chiral molecules. 3. An application in pheromone synthesis: preparation of sulcatol enantiomers. J. Org. Chem. (1987), 52, 256–260.

Bevan, S. and Szolcsanyi, J. Sensory neuron–specific actions of capsaicin: mechanisms and applications. Trends Neurosci. (1990), 11, 330–333.

Bevan, S., Hothi, S., Hughes, G., James, I.F., Rang, H.P., Shah, K., Walpole, C.S.J. and Yeats, J.C. Capsazepine: a competitive antagonist of the sensory neurone excitant capsaicin. Br. J. Pharmacol. (1992), 107, 544–552.

Bhatt, M.V. and Kulkarni, S.U. Cleavage of ethers. Synthesis (1983), 249–282.

Caterina, M.J., Schumacher, M.A., Tominaga, M., Rosen, T.A., Levine, J.D. and Julius, D. The capsaicin receptor: a heat–activated ion channel in the pain pathway. Nature (1997) 389, 816–824.

Cholewinski, A., Burgess, G.M. and Bevan, S. The role or calcium in capsaicin–induced desensitization in rat cultured dorsal root ganglion neurons. Neurosci. (1993), 55, 1015–1023.

Crout, D.H.G., Dalton, H., Hutchinson, D.W. and Miyagoshi, M. Studies on pyruvate decarboxylase: Acyloin formation from aliphatic, aromatic and heterocyclic aldehydes. Journal of the Chemical Society. Perkin transactions I (1991), 1329–1334.

Dedov, V.N. and Roufogalis, B.D. Rat dorsal root ganglion neurones express different capsaicin–evoked $Ca^{2+}$transients and permeabilities to $Mn^{2+}$. Neuroscience letters (1998) 248, 151–154.

Denniff, P., Macleod, I. and Whiting, D.A. Syntheses of the (÷)–[n]–gingerols (pungent principles of ginger) and related compounds through regioselective aldol condensations: Relative pungency assays. J. Chem Soc. Perkin I (1981), 82–87.

Duke, C.C. and Wells, R.J. Investigation of readily available chiral compounds for preparative scale resolutions. Aust. J. Chem. (1987), 40, 1641–1654.

(List continued on next page.)

*Primary Examiner*—Sreeni Padmanabhan
(74) *Attorney, Agent, or Firm*—Piper Rudnick LLP; Steven B. Kelber

(57) ABSTRACT

A compound of formula (I), a pharmaceutically acceptable derivative thereof, wherein Ph is a phenyl radical $R_1$ is H, OH, $OC_{1-4}$alkyl, $NO_2$; $R_2$ is OH, $OC_{1-4}$alkyl, OC═$OC_{1-4}$alkyl or OC═OPh where the Ph can be optionally substituted by halogen, $C_{1-3}$ alkyl or NO2; $R_1$ and $R_2$ along with the two carbon atoms of the phenyl ring to which they are attached can combine to form a 5 or 6 membered heterocyclic ring comprising 1 or 2 heteroatoms selected from O, S or N; $R_3$ is an optionally substituted hydroycarby radical; $R_4$ is H, $CH_3$, OH or ═O; when $R_4$ is ═O, then the carbon to which $R_4$ is attached is not bonded to H; W is C(═O)—$CH_2$, CH═CH—, $CH_2CO$, CH(OH)—$CH_2$, $C(CH_3)(OH)$ $CH_2$, $CH_2CH(OH)$, $CH_2C(CH_3)OH$, CO, CHOH, $C(CH_3)$ (OH), $CH_2$, $CH_2CH_2$; X is —CH—OH, $C(CH_3)OH$, $CH_2$, $CH(CH_3)$ or —C═O; Y is —CH—OH, $C(CH_3)OH$, $CH_2$, $CH(CH_3)$ or —C═O; provided that one of W, X or Y has an OH group.

$$(R_1, R_2)\,Ph{-}W{-}X{-}\underset{\displaystyle R_4}{\underset{|}{CH}}{-}Y{-}R_3 \qquad (I)$$

9 Claims, No Drawings

OTHER PUBLICATIONS

Faber, K. "Biotransformations in organic chemistry". 2nd Ed. (1995), 145–180.

Fitzgerald, M. Capsaicin and sensory neurones–a review. Pain (1983), 15, 109–130.

Hauser, C.R., Taylor, H.M. and Ledford, G.T. Benzylation and related alkylations of α–dimethylaminophenylacetonitrile by means of alkali amides: Dehydrocyanation of products to form enamines. J. Am. Chem. Soc. (1960), 82, 1786–1789.

Hikino, H., Kiso, Y., Kato, N., Hamada, Y., Shioiri, T., Aiyama, R., Itokawa, H., Kiuchi, F. and Sankawa, U. Antihepatotoxic actions of ginerols and diarylheptanoids. J. Ethnopharmacol. (1985), 14, 31–39.

Imamura, M., Smith, N.C.E., Garbarg, M. and Levi, R. Histamine $H_3$–receptor–medicated inhibition of calcitonin gene–related peptide release from cardiac C fibers. A regulatory negative–feedback loop. Circul. Res. (1996), 78, 863–869.

Kobayashi, M., Ishida, Y., Shoji, N. and Ohizumi, Y. Cardiotonic action of [8]–gingerol, an activator of the $Ca^{++}$–pumping adenosine triphosphatase of sarcoplasmic reticulum, in guinea pig atrial muscle. J. Pharmacol. Exper. Ther. (1988), 246, 667–673.

Kobayashi, M., Shoji, N. and Ohizumi, Y. Gingerol, a novel cardiotonic agent, activates the $Ca^{2+}$–pumping ATPase in skeletal and cardiac sarcoplasmic reticulum. Biochim. Biophys. Acta (1987), 903, 96–102.

Kimura, I., Pancho, L–R., Shioiri, T. and Kimura, M. Suppression of spontaneous calcium spikes and contraction in isolated portal veins of mice by gingerols and chemically related compounds. Japan J. Pharmacol. (1988), 48, 257–262.

Masuda, T., Jitoe, A. and Mabry, T.J. Isolation and structure determination of cassumunarins A, B, and C: new anti–inflammatory antioxidants from a tropical ginger, Zingiber cassumunar. J. Am. Oil Chem. Soc. (1995), 72, 1053–1057.

Mitsubishi Chemical Industries Co., Ltd. Gingerols as cardiotonic agents. Jpn. Kokai Tokkyo Koho JP 82 59,809, 10 Apr. 1982, 4 pp. (Chemical Abstracts (1982), 97:33378k).

Miyashita, M., Yoshikoshi, A. and Grieco, P.A. Pyridinium ρ–toluenesulfonate. a mild and efficient catalyst for the tetrahydropyranylation of alcohols. J. Org. Chem. (1977), 42, 3772–3774.

Munsiff, A.V., Chander, P.N., Levine, S. and Stier Jr., C.T. The lipoxygenase inhibitor phenidone protects against proteinuria and stroke in stroke–prone spontaneously hypertensive rats. Am. J. Hypertens. (1992), 5, 56–63.

Mustafa, T., Srivastava, K.C. and Jensen, K.B. Drug development report (9): Pharmacology of ginger, *Zingiber officinale*. J. Drug Dev. (1993), 6, 25–39.

Nomura, H. The pungent principles of ginger. Part I. A new ketone, zingerone (4–hydroxy–3–methoxyphenylethyl methyl ketone) occurring in ginger. J. Chem. Soc. (1917), 111, 769–776.

Noyori, R. and Takaya, H. BINAP: An efficient chiral element for asymmetric catalysis. Accounts of Chemical Research (1990), 23, 345–350.

Onogi, T., Minami, M., Kuraishi, Y. and Satoh, M. Capsaicin–like effect of [6]–shogaol on substance P–containing primary afferents or rats: A possible mechanism of analgesic action. Neuropharmacology (1992), 31, 1165–1169.

Roderick, P.J., Wilkes, H.C. and Meade, T.W. The gastrointestinal toxicity of aspirin: an overview of randomised controlled trials. British J. Clin. Pharmacol. (1993), 35, 219–226.

Salmo, R. Treatment guidelines for hypertension criticized. Pharmacy Times, Jan. 1995, 28–33.

Sawamura, S., Mizuta, T. and Shirakami, Y. Cardiotonics containing gingerol derivatives. (Nippon Kokan Kk) Jpn. Kokai Tokkyo Koho JP 0640895 [94,40,895], 5 pp (Chemical Abstracts (1994) 121:26913s).

Suekawa, M., Ishige, A., Yuasa, K., Sudo, K., Aburada, M. and Hosoya, E. Pharmacological studies on ginger. I. Pharmacological actions of pungent constituents, (6)–gingerol and (6)–shogaol. J. Pharmacobio–Dyn. (1984), 7, 836–848.

Suekawa, M., Sone, ., Sakakibara, I., Ikeya, Y., Aburada, M. amd Hosoya, E. Pharmacological studies on ginger. V. Pharmacological comparison between [6]–shogaol and capsaicin. Nippon Yakurigaku Zasshi (1986), 88, 339–347.

Takeda, S., Aburada, M., Asami, A., Ishihara, K., Fujiwara, T. and Ichikawa, Y. Preparation of 1–(4–hydroxy–3–methoxyphenyl)–4–decen–3–01 from [6]–shogoal as 5–lipoxygenase inhibitor. (Tsumura and Co., Japan) WO9215543, 24 pp (Chemical Abstracts (1993) 118:124194).

Tanaka, M., Urano, F. and Tani, T. Phenolic ketone derivatives. (Wako Pure Chemical Industries, Ltd., Japan; Tsumura Juntendo, Inc.). Jpn. Kokai Tokkyo Koho JP 61134338, 10 pp (Chemical Abstracts (1987), 106:4657).

Tran, V.H. Structure–activity relationship and cardioactivity of phenolic substances acting on $Ca^{2+}$ATPases. PhD Thesis, University of Sydney (1997).

Triggle, D.J. Cellular calcium metabolism: Activation and antagonism. J. Asthma (1984), 21, 375–385.

Vincenzi, F.F. Calmodulin pharmacology. Cell Calcium (1981), 2, 387–409.

Turner, N.J. Asymmetric synthesis using enzymes and whole cells. In "Advanced asymmetric synthesis", edited by Stephenson, G.R. (1996), 260–274.

Wood, J.N., Winter, J., James, I.F., Rang, H.P., Yeats, J. and Bevan, S. Capsaicin induced ion fluxes in dorsal root ganglion cells in culture. Journal of Neuroscience (1998), 8, 3208–3220.

Wrigglesworth, R., Walpole, C.S.J., Bevan, S., Campbell, E.A., Dray, A., Hughes, G.A., James, I., Masdin, K.J. and Winter, J. Analogues of Capsaicin with Agonist activity as Novel Analgesic Agents: Structure–Activity Studies. 4. Potent, Orally active analgesics. J. Med. Chem. (1996), 39, 4942–4951.

Yamahara, J., Hatakeyama, S., Taniguichi, K., Kawamura, M. and Yoshikawa, M. Stomachic principles in ginger. II. Pungent and anti–ulcer effects of low polar constituents isolated from ginger, the dried rhizoma of *Zingiber officinale*Roscoe, cultivated in Taiwan. The absolute stereostructure of a new diarylheptanoid. Yakugaku Zasshi (1992), 112, 645–655.

Yoshikawa, M., Hatakeyama, S., Taniguchi, K., Matuda, H. and Yamahara, J. [6]–Gingesulfonic acid, a new anti–ulcer principle, and gingerglycolipids A, B and C, three new monodiacylgalactosylglycerols from Zingiberis rhizoma originating in Taiwan. Chem. Pharm. Bull. (1992), 40, 2239–2241.

Young–Joon Surh and Sang Sup Lee. Enzymatic reduction of [6]–gingerol, a major pungent principle of ginger, in the cell–free preparation of rat liver. Life Sciences (1994), 54, PL 321–326.

Surh, Y–J and Lee, S.S. Enzymatic reduction of shogaol: A novel biotransformation pathway for the α,β–unsaturated ketone system. Biochemistry International (1992), 27, 179–187.

Lee, S.S., Re–Examination of 6–Shogaol Biotransformation by Aspergillus niger Arch. Pharm. Res. (1995), 18, 136–137.

Takahashi, H., Hashimoto, T., Noma, Y. and Asakawa Y. Biotransformation of 6–Gingerol and 6–Shogaol by Aspergillus Niger. Phytochemistry (1993), 34, 1497–1500.

Surh, Y–J., and Lee, S.S. Enzymatic Reduction of Xenobiotic α,β–Unsaturated Ketones: Formation of Allyl Alcohol Metabolites from Shogaol and Dehydroparadol. Research Communications in Chemical Pathology and Pharmacology (1994), 84, 53–61.

MEDICINAL USES OF PHENYLAIKANOLS AND DERIVATIVES

This application is a 371 of PCT/AU98/00870 filed Oct. 20, 1998.

TECHNICAL FIELD

The present invention relates to the use of phenylalkanols (gingerol analogues) in the treatment or prophylaxis of diseases by the inhibition of platelet aggregation. The present invention further relates to the use of phenylalkanols (gingerol analogues) in the treatment or prophylaxis of pain by action on sensory nerves and/or through anti-inflammatory action.

BACKGROUND ART

Agents directly or indirectly controlling calcium are potentially useful for the treatment of congestive heart failure, hypertension, pain, diabetes and cancer (Vincenzi, 1981) or may have cardioprotective or neuroprotective properties. Other agents of interest are those known to affect calcium channel mediated $Ca^{2+}$ uptake into cells, such as the therapeutic 1,4-dihydropyridine drug nifedipine and verapamil (Triggle, 1984). They are useful antianginal drugs as well as antihypertensives. Agents that have anti-inflammatory properties and antiplatelet properties are potentially useful for the treatment of inflammation, pain, stroke and ischaemic diseases.

The gingerols are a series of natural homologues isolated from ginger, *Zingiber officinale*. Gingerols are classified according to their alkyl chain length eg. [6]-gingerol, [8]-gingerol (Deniff et al, 1981). A patent is published (Takeda et al, 1992) on the preparation of racemic gingerols (eg. [6]-gingerol) and their dehydrated derivatives (eg. [6]-shogaol) and their use as antipyretic and analgesic agents (no data). Another patent is published (Tanaka et al, 1987) on a shogaol derivative where the carbonyl group of the side-chain is reduced to hydroxy group and its use in the treatment of thrombosis and pain.

Agents that inhibit platelet aggregation may be used for the treatment of cardiovascular diseases and stroke. Platelets play an essential role in blood clotting at sites of wound injury, but unwanted activation of platelets in the circulation can give rise to thrombus formation, and is implicated in the onset of stroke, myocardial infarction, and other diseases. Therapeutic modalities aimed at secondary prevention of stroke and ischaemic diseases include vascular surgery, anticoagulant and platelet aggregation inhibition. Among these, the platelet aggregation inhibition appears to be the most promising because in fast-flowing vessels thrombi are composed mainly of platelets with little fibrin. Recent clinical trials have indicated that antiplatelet therapy protects a wide range of patients at high risk of occlusive vascular disease (Antiplatelet Trialists' Collaboration, 1994). Medium dose aspirin is the most widely used antiplatelet regimen, and no other regimen appeared significantly more effective at preventing myocardial infarction and stroke. However, gastrointestinal tract upset, particularly peptic ulcer, is a common problem associated with the use of aspirin (Roderick, 1993). In addition, complications in some disease conditions such as diabetes and asthma are of major concern in the use of aspirin. A new safe antiplatelet therapy is therefore required.

There is a need for safe and effective agents for the treatment of pain and inflammation, particularly arthritis. The use of analgesics such as non-steroidal anti-inflammatory agents (NSAIDS), paracetamol and morphine still remain a primary therapy for such conditions. Each of these agents, however, has limitations. Aspirin and newer non-steroidal anti-inflammatory agents can cause gastrointestinal discomfort and eventually the development of peptic ulcer. Paracetamol may produce liver and kidney toxicity with chronic use. Morphine, though effective, can be addictive and exhibit tolerance. Recently, a topical analgesic has been developed from capsaicin for control of pain (anti-nociception). Capsaicin has also been used extensively for research in neurosciences, where it has benefit in the modulation of sensory nerve activity (nerves which transmit sensations of pain-causing stimuli from the periphery to the brain). Capsaicin has also yielded important knowledge about pain pathways. However, capsaicin is an irritant and cannot be administered systemically because of its potential to cause neuro-inflammation. Its use as a topical agent is also limited for several reasons: it causes mild to moderate burning sensation, erythema and stinging after application; severe irritation to sensitive organs such as eyes; it cannot be used on broken or irritated skin; excessive inhalation of aerosolised dried cream may cause coughing, which is the most commonly reported systemic side-effect associated with the use of capsaicin preparations. Higher doses may produce neurotoxic effects through mechanisms not completely understood. Development of more effective anti-nociceptive agents is imperative.

Stroke and ischaemic diseases that afflict millions of people world-wide, are among the most common maladies affecting people in industrialised countries. Current efforts directed at reducing the morbidity and mortality of these disease conditions are aimed at both relief and preventative therapies. The platelet aggregation inhibition appears to be the most promising modality aimed at prevention of stroke and ischaemic diseases because in fast-flowing vessels thrombi are composed mainly of platelets with little fibrin.

There is great need to develop more effective drugs with novel action. Substances that are the subject of the present invention are typically substances that exert useful medicinal actions through mechanisms where calcium is either directly or indirectly involved. For example, hypertension including stroke are common disorders with extremely high mortality rate. Their incidence is steadily increasing despite a substantial haemostasis improvement by a number of therapeutic regiments (Salmo, 1995).

DISCLOSURE OF THE INVENTION

In one aspect, the present invention provides a compound of formula (I), a pharmaceutically acceptable derivative thereof:

(I)

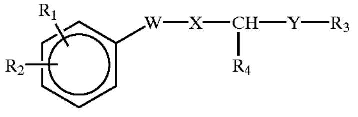

where

- $R_1$ is H, OH, $OC_{1-4}$alkyl, $NO_2$
- $R_2$ is OH, $OC_{1-4}$alkyl, OC=$OC_{1-4}$alkyl or OC=OPh where the Ph can be optionally substituted by halogen, $C_{1-3}$ alkyl or $NO_2$;
- $R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O;

provided that one of W, X or Y has an OH group and provided that when (1) $R_1$ is $OC_{1-4}$alkyl, $R_2$ is OH or OAcyl, W=$CH_2CH_2$ and X=C=O, $R_3$ is $C_{2-12}$ alkyl, $R_4$ is H, then Y is not CHOH (gingerols) (Mustafa et al, 1993);

(2) $R_1$ is $OCH_3$, $R_2$ is OH, W is $CH_2CH_2$, $R_3$ is $C_5$ or $C_7$ alkyl, $R_4$ is H and X=CHOH then Y is not CHOH (gingerdiol) (Mustafa et al, 1993);

(3) $R_1$ is $OCH_3$, $R_2$ is OH, W is CH=CH, $R_3$ is $C_{2-12}$ alkyl, $R_4$ is H and X is C=O, then Y is not CHOH (dehydrogingerols);

(4) $R_1$ is $OCH_3$, $R_2$ is OH, W=$CH_2CH_2$, X is CHOH, $R_4$ is H and $R_3$ is $C_5$ alkyl then Y is not $CH_2$ (reduced paradol) (Young-Joon et al, 1992);

(5) $R_1$ is $OCH_3$, $R_2$ is OH, W=$CH_2CH_2$, X is C=O, $R_4$ is H then Y is not $C(OH)CH_3$ (Sawamura et al).

(6) $R_1$ is $OC_{1-4}$ alkyl, $R_2$ is OH or OAcyl, W=CH=CH and X=C=O, $R_3$ is $C_{2-8}$ alkyl, $R_4$ is H, then Y is not CHOH ([4]-[10]-dehydrogingerols) (Denniff et al, 1981);

(7) $R_1$=$R_2$ is OH, W=$CH_2CH_2$ and X=C=O, $R_3$ is $C_{4,6}$ alkyl, $R_4$ is H, then Y is not CHOH ([6]- and [8]-norgingerols) (Terumo Corporation, 1992; Meiji, 1989);

8) $R_1$=$R_2$ is OH, W=CH=CH and X=C=O, $R_3$ is $C_6$ alkyl, $R_4$ is H, then Y is not CHOH ([8]-nordehydrogingerols) (Terumo Corporation, 1992);

(9) $R_1$ is $OC_{1-4}$ alkyl, $R_2$ is OH or OAcyl, W=$CH_2CH_2$ and X=C=O, $R_3$ is $C_{2,4,6}$ alkyl, $R_4$ is H, then Y is not C=O ([4]-, [6]- and [8]-gingerdiones) (Denniff et al, 1981); (Terumo Corporation, 1992);

(10) $R_1$ is $OC_{1-4}$ alkyl, $R_2$ is OH or OAcyl, W=CH=CH and X=C=O, $R_3$ is $C_{2,4,6}$ alkyl, $R_4$ is H, then Y is not C=O ([4]-, [6]- and [8]-dehydrogingerdione) (Denniff et al, 1981); (Terumo Corporation, 1992);

(11) $R_1$=$R_2$ is OH, W=$CH_2CH_2$ and X=C=O, $R_3$ is $C_6$ alkyl, $R_4$ is H, then Y is not C=O ([8]-norgingerdione) (Terumo Corporation, 1992-EP516082);

(12) $R_1$=$R_2$ is OH, W=CH=CH and X=C=O, $R_3$ is $C_6$ alkyl, $R_4$ is H, then Y is not C=O ([8]-nordehydrogingerdione) (Terumo Corporation, 1992);

(13) $R_1$=$R_2$ is OH, W=$CH_2CH_2$ and X=C=O, $R_3$ is $C_{2-12}$ alkyl, $R_4$ is H, then Y is not CHOH (norgingerols) (Terumo Corporation, 1992; Meiji, 1989; Merrell Dow Pharmaceuticals, 1992-EP516082);

(14) $R_1$ is $OC_{1-4}$ alkyl or OH, $R_2$ is OH, W is $CH_2CH_2$, $R_3$ is $C_{2-12}$ alkyl, $R_4$ is H and X is CHOH, then Y is not CHOH (gingerdiols or norgingerdiols) (Merrell Dow Pharmaceuticals-EP516082).

In a second aspect, the present invention provides the use of a compound of formula (I):

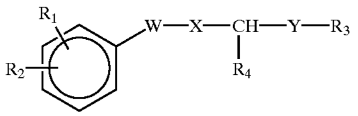

(I)

where $R_1$ is H, OH, $OC_{1-4}$alkyl, $NO_2$ $R_2$ is OH, $OC_{1-4}$alkyl, OC=$OC_{1-4}$alkyl or OC=OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

is $R_3$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O;

provided that one of W, X or Y has an OH group a pharmaceutically acceptable derivative thereof in the treatment or prophylaxis of diseases by the inhibition of platelet aggregation.

In a third aspect, the present invention provides the use of a compound of formula (I):

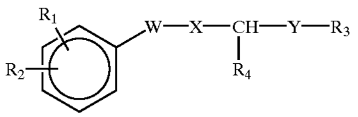

(I)

where $R_1$ is H, OH, $OC_{1-4}$alkyl, $NO_2$ $R_2$ is OH, $OC_{1-4}$alkyl, OC=$OC_{1-4}$alkyl or OC=OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)$ (OH), $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O;

provided that one of W, X or Y has an OH group a pharmaceutically acceptable derivative thereof in the manufacture of a medicament for the treatment or prophylaxis of diseases by the inhibition of platelet aggregation.

In a fourth aspect, the present invention provides a pharmaceutical formulation comprising a compound of formula (I):

(I)

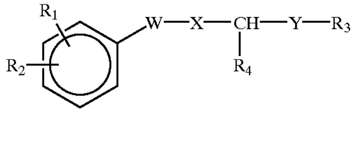

where $R_1$ H, OH, $OC_{1-4}$alkyl, $NO_2$ $R_2$ is OH, $OC_{1-4}$alkyl, $OC{=}OC_{1-4}$alkyl or OC=OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_1$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O;

provided that one of W, X or Y has an OH group a pharmaceutically acceptable derivative thereof in a pharmaceutically acceptable carrier.

In a fifth aspect, the present invention provides novel compounds as follows 1-(4-hydroxy-3-methoxyphenyl)dodecan-3-ol
1-(4-hydroxy-3-methoxyphenyl)dodecan-5-ol
3-methyl-1-(4-hydroxy-3-methoxyphenyl)undecan-3-ol
3-methyl-1-(4-hydroxy-3-methoxyphenyl)tridecan-3-ol
3-hydroxy-1-(4-hydroxy-3-methoxyphenyl)dodecan-5-one
3-hydroxy-1-(4-hydroxy-3-methoxyphenyl)decan-1-one
3-hydroxy-1-(4-hydroxy-3-methoxyphenyl)dodecan-1-one
1-hydroxy-1-(4-hydroxy-3-methoxyphenyl)undecan-2-one
2-hydroxy-1-(4-hydroxy-3-methoxyphenyl)undecan-1-one
5-hydroxy-1-(2-hydroxy-3-methoxyphenyl)dodecan-3-one ([8]-orthogingerol)
5-hydroxy-1-(4-hydroxyphenyl)decan-3-one
5-hydroxy-1-(4-hydroxyphenyl)dodecan-3-one
5-hydroxy-1-(4-hydroxyphenyl)dodecan-1-ene-3-one
5-hydroxy-1-(3,4-methylenedioxyphenyl) dodecan-3-one
5,12-dihydroxy-1,16-bis(4-hydroxy-3-methoxyphenyl) hexadecane-3,14-dione (a bis compound)
1-(4-hydroxy-3-methoxyphenyl)dodecane-1,4-diene-3-one.
2-hydroxy-1-(3,4-dimethoxyphenyl)dodecan-3-one
2-hydroxy-1-(3,4-dimethoxyphenyl)undecan-4-one
1-(3,4-dimethoxyphenyl)dodecan-2-ol All alkyl, alkenyl, alkynyl, alkylene, alkenylene and alkynylene carbon chains can be straight or branched chain.

Halogen includes bromo, chloro, fluoro or iodo.

Pharmaceutically acceptable derivatives include acid addition salts.

In a further aspect, the present invention provides the use of a compound of formula (I) according to the second aspect of the present invention in the treatment or prophylaxis of pain by action on sensory nerves and/or through anti-inflammatory action and/or through neurokinin inhibitory action.

Preferably, the use of a compound of formula (I) in the treatment or prophylaxis of pain by action on sensory nerves is as an analgesic.

In another aspect, the present invention provides the use of a compound of formula (I) according to the second aspect of the present invention in the treatment or prophylaxis of cardiovascular disease.

In yet another aspect, the present invention provides a process for preparing the following compounds

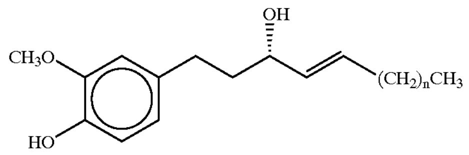

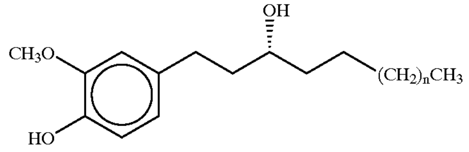

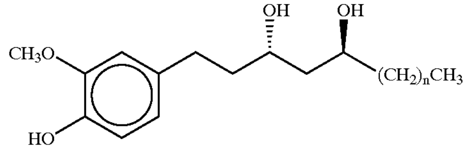

which comprises treating ginger extract with heat 10 and/or acid and then followed by treatment with a microorganism or enzyme.

MODES FOR CARRYING OUT THE INVENTION

Starting materials for preparing compounds of formula (I) are commercially available or are prepared according to literature procedures.

The following description provides methods of preparing compounds of formula (I).

(1) when W is —CH═CH—, X is C═O, Y is —CHOH— and $R_3$ is alkyl, alkenyl or alkynyl (i) treating the appropriate benzaldehyde with acetone (ii) protecting any hydroxy groups (iii) treating the resulting compound with an appropriate aliphatic aldehyde in the presence of LDA as follows

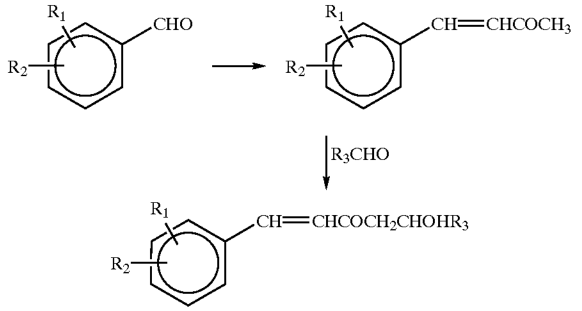

and deprotecting as necessary;

(2) when W is —$CH_2CH_2$—, X is C═O, Y is —CHOH— and $R_3$ is alkyl or where $R_3$ is a linking group of a bis compound and $R_3$ is alkylene reducing the product obtained in (1) above;

or when $R_3$ is alkyl, alkenyl or alkynyl or where $R_3$ is a linking group of a bis compound and $R_3$ is alkenylene or alkynylene reducing the intermediate ketone compound from (1) above before condensation with the appropriate aldehyde as follows:

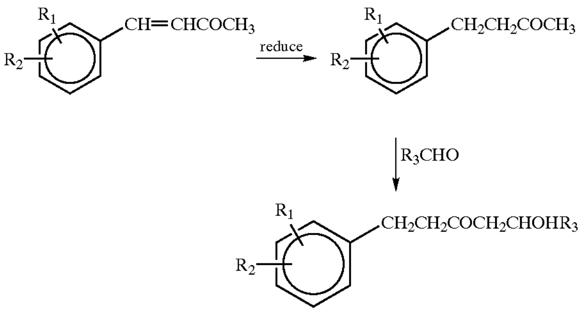

(3) when W is CH═CH, X is CHOH and Y is C═O starting with the appropriate cinnamaldehyde and reacting to protect any hydroxy groups if necessary and then treating with appropriate ketone in LDA as follows

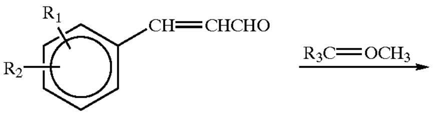

-continued

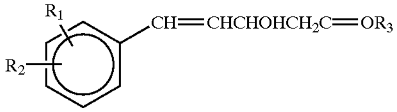

and deprotecting as necessary;

(4) when W is $CH_2CH_2$, X is CHOH, Y is C═O and $R_3$ is alkyl reducing the product of (3) above;

or when $R_3$ is alkyl, alkenyl or alkynyl starting with the appropriate cinnamaldehyde and reducing as for (2) above before condensation with the appropriate ketone or alternatively oxidising the appropriate alcohol followed by condensation with the appropriate ketone as follows

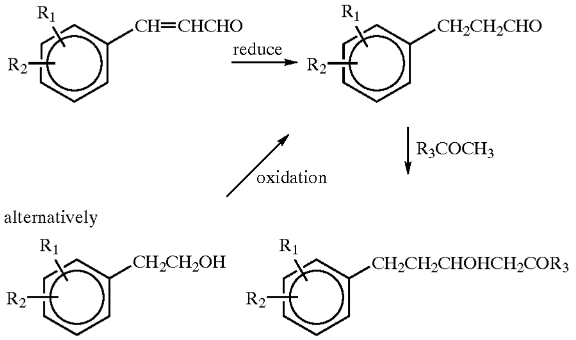

5) when W is C(═O)—$CH_2$, X is CHOH and Y is $CH_2$ starting with the appropriate acetophenone compound and protecting any hydroxy groups if necessary and treating with the appropriate aldehyde compound as follows

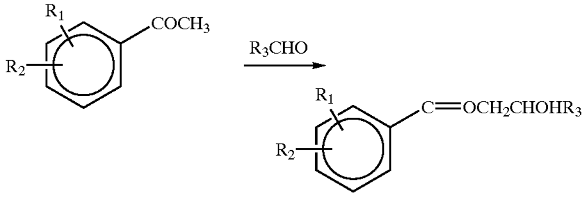

and deprotecting as necessary (6) when W is $CH_2$, X is CO and Y is CHOH

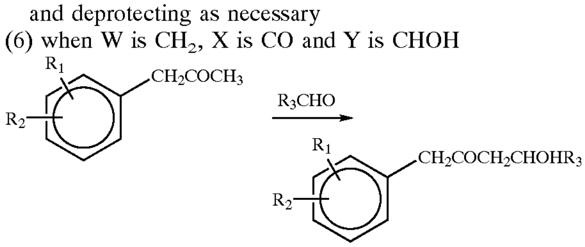

(7) when W is $CHOHCH_2$, X is CO and Y is $CH_2$

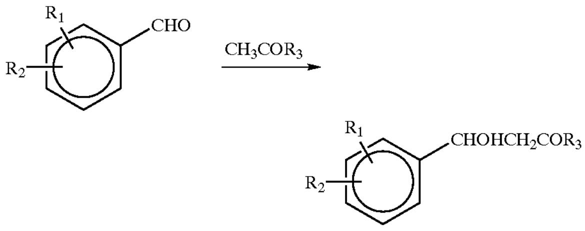

(8) when W is $CH_2$, X is CHOH and Y is CO

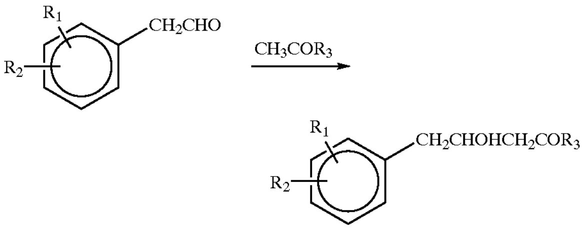

Substances with the α-hydroxyketone group may be prepared by the following general procedure (Organic Syntheses 3, 562)

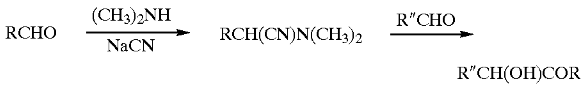

(9) when W is CO and $COCH_2$, X is $CH_2$ and Y is CHOH

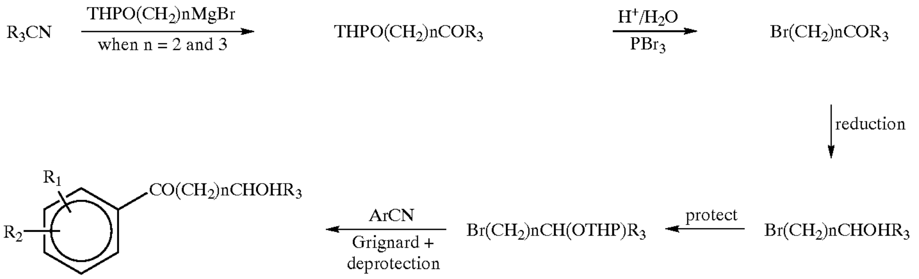

(10) when W is $CH_2CO$, X is $CH_2$ and Y is CHOH

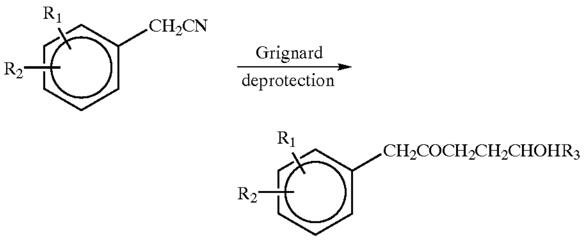

(11) when W is CHOH and $CHOHCH_2$, X is $CH_2$ and Y is C═O

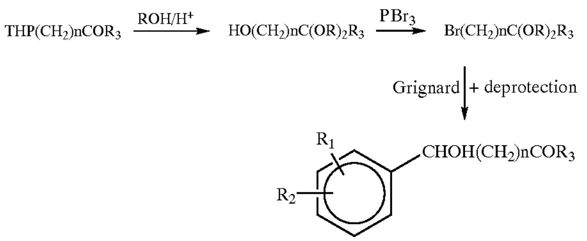

(12)when W is $CH_2CHOH$, X is $CH_2$ and Y is CO

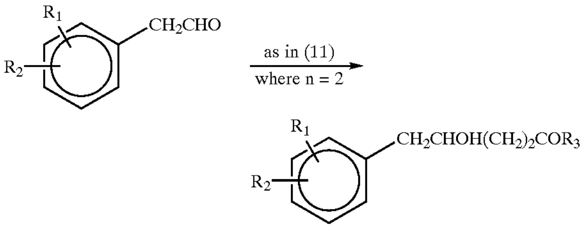

(13) when W is CO, X is CHOH and Y═$CH_2$

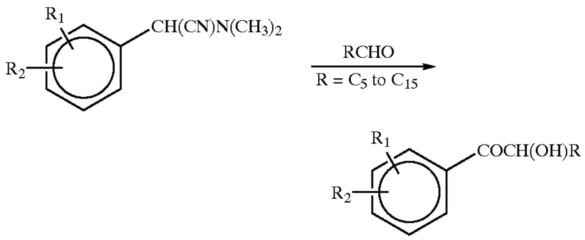

(14) when W is $CH_2CO$, X is CHOH and Y is $CH_2$

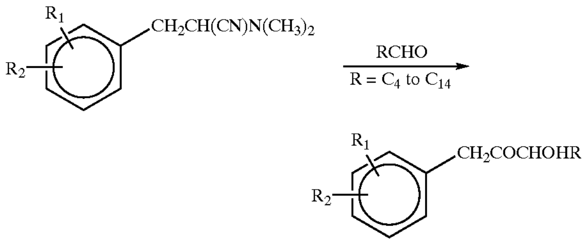

(15) when W is CHOH, X is CO and Y is $CH_2$

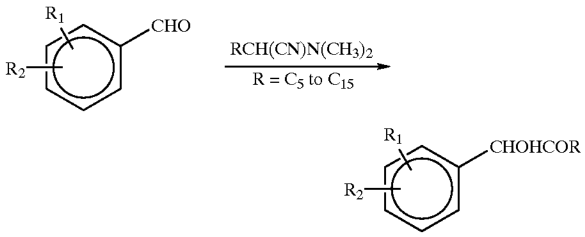

(16) when W is $CH_2CHOH$, X is CO and Y is $CH_2$

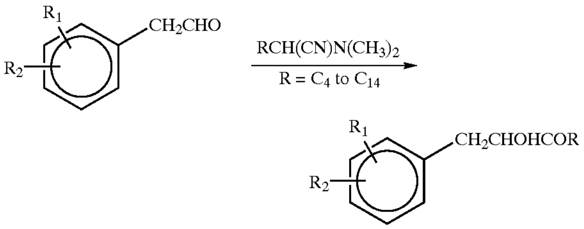

(17) when W is $CH_2$, $CH_2CH2$ or other having an OH group, Y is CHOH or CH2 and X is $CH_2$ or CHOH but one of W, X or Y has an OH group

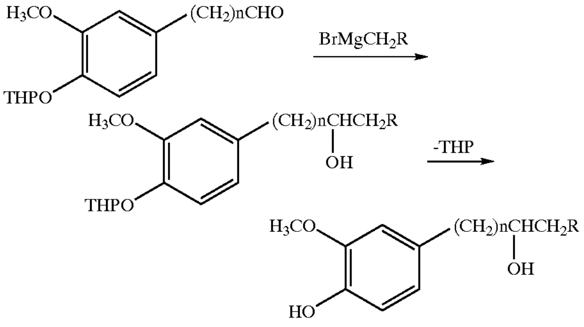

or alternatively when W does not have an OH group and X is CHOH or CH, and Y is CHOH or $CH_2$ but one of X or Y is CHOH

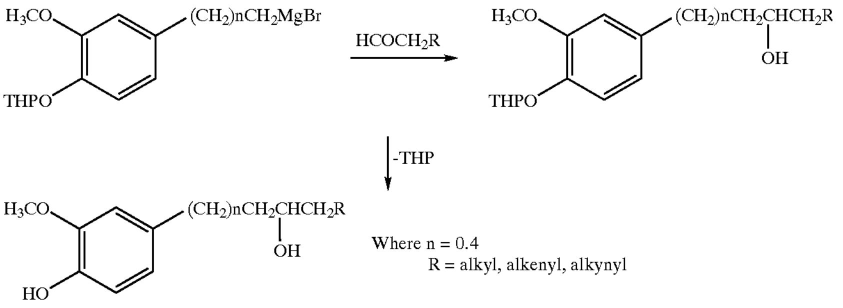

(18) when W is CHOH or $CH_2CHOH$, X is $CH_2$ and Y is $CH_2$

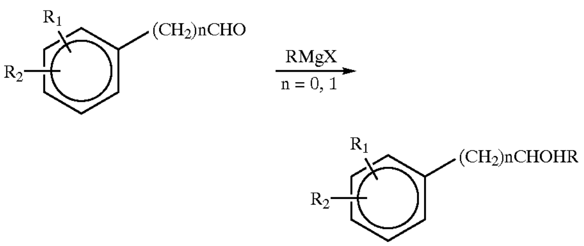

(19) when W is $CH_2CH_2$, X is CHOH and Y is $CH_2$, then in the formula in (18) n=2;

(20) when W is $CH_2$ or $CH_2CH_2$, and X is $CH_2$ and Y is CHOH then in the formula in (18) n=3 or 4.

For Grignard or similar condensation, the aldehyde can be replaced with the methyl ketone to give the methyl branched product.

In the preparation of α-hydroxyketones the cyanohydrin may be prepared from a methylketone.

Reduction steps are typically carried out with hydrogen using a suitable catalyst such as Pd/C or with $NaBH_4$ or $NaCNBH_3$.

Oxidation steps are typically carried out using pyridinium chlorochromate.

Protecting groups are typically tetrahydropyran (THP) or acyls.

Asymmetric Synthesis of Gingerol Analogues

Asymmetric synthesis of the gingerol and analogues can be achieved either by organic chemistry or enzyme-catalysed reaction. The most attractive features of using enzymes in asymmetric synthesis are that enzymes are inherently chiral and have ability to catalyse reactions with high selectivity leading to the synthesis of single stereoisomers. The asymmetric transformation of a prochiral ketone group (shown in reaction scheme below) into highly optical pure R- or S-isomer can be achieved either by organic synthesis or enzyme-catalysed reaction. In organic synthesis, R- or S-isomer can be exclusively formed by catalytic hydrogenation catalysed by an enantiomeric form of transition metal complexes. In the present invention ruthenium (R)-(+)-BINAP and ruthenium (S)-(−)-BINAP complexes will be employed as chiral catalysts (Noyori and Takaya, 1990). Alternatively, R- and S-isomer of the gingerol analogues can be formed by enzyme-catalysed reduction. In this case a separate enzyme system can be employed to produce optically pure enantiomers. Two enzyme systems that can be used in this reaction are *Aspergillus niger* and *Thermoanaerobium brockii* alcohol dehydrogenase (Belan, et al, 1987), (Faber, 1995; Turner, 1996) as shown in the reaction scheme below.

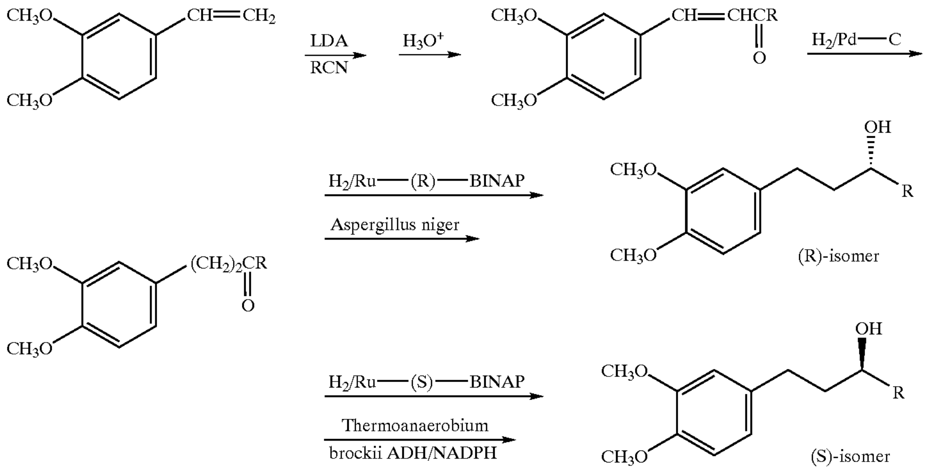

Asymmetric Synthesis of Capsaicin-like Analogues

Asymmetric synthesis of capsaicin-like analogues can be achieved by the condensation of an aldehyde with an α-ketoacid. The reaction is known as acyloin condensation which is effectively catalysed by an enzymatic system, pyruvate decarboxylase (Crout, et al. 1991), (Faber, 1995; Turner, 1996). The advantage of using this enzyme is a remarkable tolerance by the enzyme system with respect to a range of structures of the aldehyde. More significantly from a synthetic point of view, the α-hydroxyketone compounds can be converted chemically or enzymatically into the corresponding dione or chiral diol compounds.

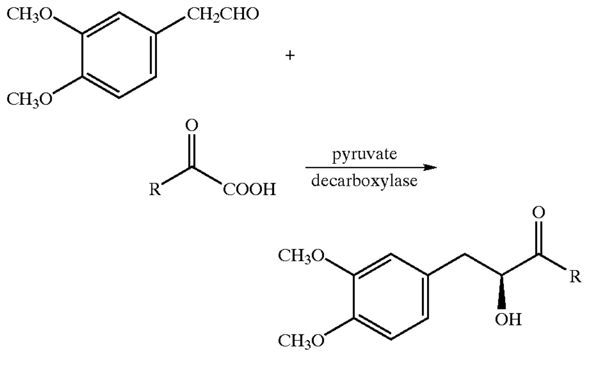

R can be: alkyl, alkenyl, alkynyl, phenylalkyl, phenylalkenyl, phenylalkynyl, etc. R may have methyl branches and/or substitutions.

Transformation of Ginger Preparations, Gingerols, Gingerol Analogues and Related Substances Using Enzymes or Micro-organisms to Produce Therapeutically Useful Products Ginger extract contains numerous phenolic substances. Many of these substances are present as optically pure isomers, for example, [6]- and [8]-gingerols, the most abundant pungent components present in fresh ginger extract have been identified as the (−)-(S)-isomers. Gingerols possess a β-hydroxy keto functional group which makes them vulnerable to degradation by dehydration to form shogaols. This degradation perhaps is the major cause of loss in potential therapeutic effect of gingerols and the variations and changes in therapeutic effects of ginger preparations. The degradation of gingerol, however, results in the formation of the biologically active component, shogaol, which has different pharmacological activities to gingerol. This biologically active component may be enzymatically transformed into various components in ginger which are yet to be fully determined. The enzyme-catalysed conversion of [6]-shogaol in vitro using a supernatant fraction isolated from rat liver is reported to result in the formation of [6]-paradol, [6]-dehydro- and [6]-dihydroparadol. An homologue of [6]-dihydroparadol was chemically synthesised in our laboratory, namely, 1-(4-hydroxy-3-methoxyphenyl) dodecan-3-ol [3.93] which was found to have a range of therapeutically useful biological activities. The ginger extract can be treated with yeast or isolated enzyme to form dihydroshogaol, dihydroparadol, and other reduced derivatives including 1-(4-hydroxy-3-methoxyphenyl)dodecan-3-ol [3.93]. Compounds of formula (I) can also be prepared by treating the ginger extract with heat, acid, enzymes or micro-organisms, or combination or sequence thereof, to produce products that contain optimal amounts of dihydroshogaol, dihydroparadol (particularly 1-(4-hydroxy-3-methoxyphenyl)dodecan-3-ol and homologues) or other substances with similar therapeutic actions. The optimally transformed ginger extract can be used to produce therapeutically useful herbal medicines and pharmaceutical agents.

The process described above enables a more stable, potent and effective product to be derived from ginger preparations based on the therapeutically useful actions of gingerols and gingerol like substances falling within the scope of the general formula (I). This process is particularly suited to the production of herbal products.

Transformation of a Ginger Preparation Using Yeast

Yeast is a convenient source of enzymes that has been extensively exploited in asymmetric synthesis. Its enzyme-catalysed reactions are regarded as natural processes and usually occur under mild conditions and with attendant selectivity, such as chemo-, regio- and stereoselectivity, leading to the formation of naturally occurring isomers. Apart from the naturally occurring substances such as gingerols, shogaols, gingerdiols, etc. the following compounds can be produced from the ginger extract in the presence of yeast:

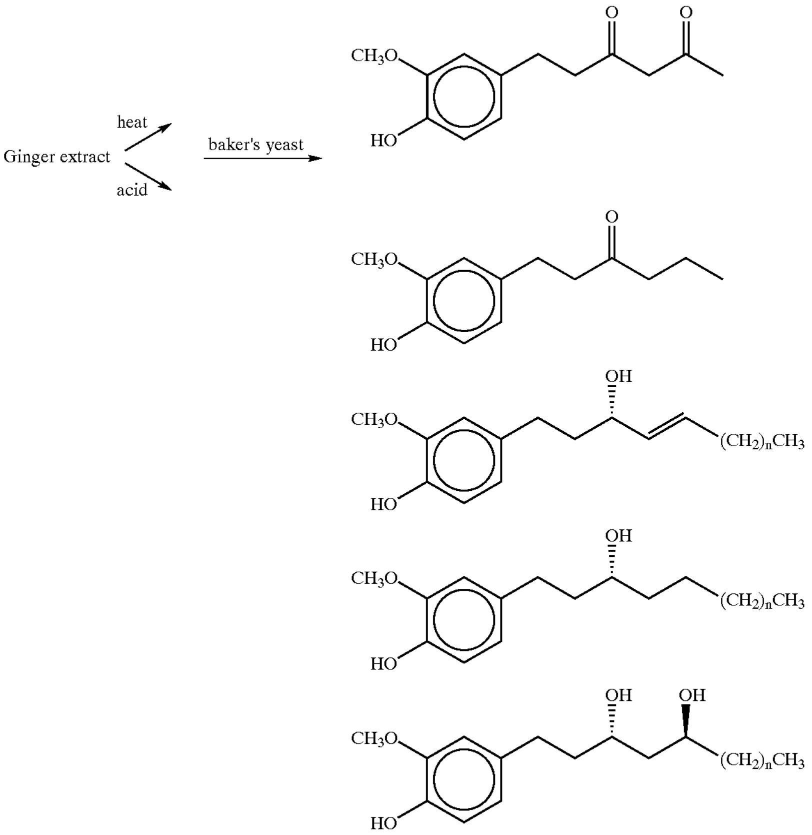

wherein n=1–10

Note: Both the baker's yeast and isolated enzyme such as *Thermoanaerobium brockii* ADH will produce naturally occurring isomers, typically the (S)-isomers (Belan, et al, 1987).

Preferably the acid is a strong acid such as HCl, $H_2SO_4$ $H_3PO_4$ and the like.

Synthetic Gingerol Analogues as Antiplatelet Agents

Racemic gingerols and about 30 analogues have been prepared by synthesis and their biological activities, particularly on the cardiovascular system, have been investigated (Tran, 1997). The gingerol analogue, 3-hydroxy-1-(4-hydroxy-3-methoxyphenyl)dodecane [3.93], was tested on a pharmacological screen with arachidonic acid as substrate in rabbit platelet-rich plasma and found to have potent anti-platelet aggregation activity, being three times more potent than the indomethacin reference compound. However, the analogue had little or no effect on bleeding time in mice. Gingerols and synthetic analogues were tested on platelet rich plasma from human blood and found to inhibit platelet aggregation.

Effects of Gingerol Analogues on Sensory Neurons

The increase in intracellular calcium level is also known to be important for capsaicin-induced desensitisation in rat cultured dorsal root ganglion neurons (Cholewinski et al, 1993) and is believed, in vivo, to give rise to an analgesic effect. Capsaicin is known to excite a subset of sensory neurons by opening non-selective cation channels (Bevan and Szolcsanyi, 1990) which preferentially allows $Ca^{2+}$ ion entry leading to pronounced desensitisation. A synthetic gingerol analogue was found to antagonise the effect of capsaicin, and vice versa, in rat mesenteric artery bed. It is proposed that gingerol and its analogues act on a so called "gingerol receptor" which previously was undefined, or on the capsaicin receptor or a subclass of capsaicin receptor. Pharmacological comparison has been made between capsaicin and [6]-shogaol, a dehydration product of [6]-gingerol (Suekawa et al, 1986). The neuropharmacological properties of gingerol and synthetic analogues may be investigated by specific measurement of $Ca^{2+}$ within the cytosol, nucleus and mitochondria or of $Ca^{2+}$ currents. Specific measurements of the action of gingerol and synthetic analogues in the sensory neurons have led to the discovery of new pharmacological agents with less pungent effect and little or no neuro-inflammatory effect compared with capsaicin which may be developed as a superior analgesic agent. These agents may be useful for the treatment of pain or conditions such as arthritis.

Anti-inflammatory Action of Gingerol Analogues

Gingerol analogues exert anti-inflammatory action through inhibition of lipoxygenase and cyclooxygenase enzymes and through their antioxidant properties (Musuda et al, 1995). The gingerol analogues may be used to treat inflammatory conditions such as arthritis and may also be used to protect against stroke (Munsiff et al, 1992).

Neurokinin-1 Receptor Activity of Gincerol Analogue

A gingerol analogue, 1-(4-hydroxy-3-methoxyphenyl) dodecan-3-ol [3.93], exhibited relatively potent inhibition of neurokinin-1 receptor (NK-1) mediated by substance P. Gingerol analogues may exert their antinociceptive and anti-inflammatory activities through this mechanism and, therefore, may be useful in the treatment of pain and inflammatory conditions such as migraine headache and internal pain.

Known Substances 5-hydroxy-1-(4-hydroxy-3-methoxyphenyl)decan-3-one ([6]-gingerol)
5-hydroxy-1-(4-hydroxy-3-methoxyphenyl)dodecan-3-one ([8]-gingerol)
5-hydroxy-1-(4-hydroxy-3-methoxyphenyl)dodecan-1-ene-3-one ([8]-dehydrogingerol)
1-(4-hydroxy-3-methoxyphenyl)dodecan-4-ene-3-one ([8]-shogaol)
1-(4-hydroxy-3-methoxyphenyl)dodecan-3-one ([8]-paradol)
1-(4-hydroxy-3-methoxyphenyl)dodecane-3,5-diol ([8]-gingerdiol)
5-hydroxy-1-(3-hydroxy-4-methoxyphenyl)dodecan-3-one ([8]-isogingerol)

New Chemical Entities 1-(4-hydroxy-3-methoxyphenyl)dodecan-3-ol
1-(4-hydroxy-3-methoxyphenyl)dodecan-5-ol
3-methyl-1-(4-hydroxy-3-methoxyphenyl)undecan-3-ol
3-methyl-1-(4-hydroxy-3-methoxyphenyl)tridecan-3-ol
3-hydroxy-1-(4-hydroxy-3-methoxyphenyl)dodecan-5-one
3-hydroxy-1-(4-hydroxy-3-methoxyphenyl)decan-1-one
3-hydroxy-1-(4-hydroxy-3-methoxyphenyl)dodecan-1-one
1-hydroxy-1-(4-hydroxy-3-methoxyphenyl)undecan-2-one
2-hydroxy-1-(4-hydroxy-3-methoxyphenyl)undecan-1-one
5-hydroxy-1-(2-hydroxy-3-methoxyphenyl)dodecan-3-one ([8]-orthogingerol)
5-hydroxy-1-(4-hydroxyphenyl)decan-3-one
5-hydroxy-1-(4-hydroxyphenyl)dodecan-3-one
5-hydroxy-1-(4-hydroxyphenyl)dodecan-1-ene-3-one
5-hydroxy-1-(3,4-methylenedioxyphenyl)dodecan-3-one
5,12-dihydroxy-1,16-bis(4-hydroxy-3-methoxyphenyl) hexadecane-3,14-dione
1-(4-hydroxy-3-methoxyphenyl)dodecane-1,4-diene-3-one
2-hydroxy-1-(3,4-dimethoxyphenyl)dodecan-3-one
2-hydroxy-1-(3,4-dimethoxyphenyl)undecan-4-one
1-(3,4-dimethoxyphenyl)dodecan-2-ol A number of structural analogues of phenolic hydroxyketones called gingerols (listed above) were prepared by synthesis. 1-(4-Hydroxy-3-methoxyphenyl)dodecan-3-ol [3.93] emerged as one of the most interesting substances. It was initially identified as the most potent inotropic agent in the guinea pig atrium and it was thought that its inotropic activity was a result of enhancing of SR $Ca^{2+}$-ATPase since it exhibited relatively potent SR $Ca^{2+}$-ATPase activation. It was found however that the positive inotropic effect in the series could be dissociated from the enhancement of SR $Ca^{2+}$ pump stimulation (Tran, 1997). This is in contrast to the previous reports (Kobayashi et al, 1988) which had led to the conclusion that the positive inotropic (increased force of contraction) effect of [8]-gingerol on the guinea pig atrium was associated with the stimulation of $Ca^{2+}$ uptake into the sarcoplasmic reticulum (SR) of cells via the SR $Ca^{2+}$ pump, thereby allowing greater $Ca^{2+}$ release (and hence force of contraction) on stimulation of the myocardium. Further work with 1-(4-hydroxy-3-methoxyphenyl) dodecan-3-ol showed that the positive inotropic effect of the compound was produced through actions on sensory nerves innervating the release of neuropeptides and possibly histamine. Most importantly, the inotropic effect of the compound was blocked by pretreatment of the atrium with capsaicin, and pretreatment of the atrium with the compound caused a loss of capsaicin inotropic effect. A putative capsaicin receptor antagonist, capsazepine (10 μM) (Bevan et al, 1992) was found to block the inotropic response to 1-(4-hydroxy-3-methoxyphenyl)dodecan-3-ol completely. These results are consistent with a mechanism whereby both capsaicin and 1-(4-hydroxy-3-methoxyphenyl)dodecan-3-ol [3.93] cause an increase in rate and force of guinea pig atria by releasing calcitonin gene related protein (cGRP) (and possibly other neuropeptides) from sensory nerves, which in turn acts directly on the atria and/or indirectly by the release of histamine (Imamura et al, 1996). However, it is not clear whether capsaicin and the compound exert their effects via the same receptor, by different subsets of capsaicin receptors or by a different pathway yet to be described. A relationship between capsaicin and 1-(4-hydroxy-3-methoxyphenyl) dodecan-3-ol is supported by a comparison of the structures of the two compounds, which are vanilloids showing significant similarities (but also differences). The inotropic activity of 1-(4-hydroxy-3-methoxyphenyl)dodecan-3-ol was shown to be enantiospecific as one enantiomer exhibited 100 fold more potent action than the other in increasing the force of contraction in guinea pig atria.

The proposed mechanism of neuropeptide release by 1-(4-hydroxy-3-methoxyphenyl)dodecan-3-ol, similar to that of capsaicin, was supported by studies in blood vessels. The compound was shown to be very potent in relaxing vasopressin-contracted rat mesenteric small arteries (200–300 μm diameter) at $10^{-8}$ to $10^{-6}$ M. This effect was antagonised by capsaicin pretreatment ($3\times10^{-7}$ M). Interestingly, this effect on relaxation of mesenteric artery could not be explained by cGRP release, using a selective cGRP antagonist, even though cGRP is known to relax this arterial bed. The potency ($EC_{50}$) of the compound for relaxation of the mesenteric artery was 100-fold greater than for the inotropic effect in guinea pig atrium. This contrasts with capsaicin which has similar activity in Guinea pig atria (force and rate) and relaxing rat mesenteric artery.

In contrast to inotropic activity of 1-(4-hydroxy-3-methoxyphenyl)dodecan-3-ol which is enantiospecific, both enantiomers showed similar potency in relaxation of rat mesenteric vascular bed. Preliminary investigation on vasodilation property of other gingerol analogues such as 3-hydroxy-1-(4-hydroxy-3-methoxyphenyl)dodecan-5-one, 5-hydroxy-1-(3,4-methylenedioxyphenyl)dodecan-3-one and [8]-paradol, all showed potency in relaxing rat mesenteric artery.

In summary, these results suggest that 1-(4-hydroxy-3-methoxyphenyl)dodecan-3-ol [3.93] acts like capsaicin to release one or more vasorelaxant substances from sensory nerves.

The gingerol analogue, 3-hydroxy-1-(4-hydroxy-3-methoxyphenyl)dodecane [3.93], was tested on a pharmacological screen with arachidonic acid as substrate in rabbit platelet-rich plasma and found to have potent antiplatelet aggregation activity, three time more potent than the indomethacin reference compound. However, the analogue had little or no effect on bleeding time in mice. Antiplatelet activity of the compound was shown to be specific for arachidonic acid as the substance did not affect platelet function either via adenosine diphosphate or thromboxane A mechanisms. It is therefore thought that the compound has interfered with arachidonic acid metabolism, probably by inhibiting cyclo-oxygenase enzyme. Gingerols and synthetic analogues were tested on platelet rich plasma from human blood and found to inhibit platelet aggregation initiated by arachlidonic acid.

3-hydroxy-1-(4-hydroxy-3-methoxyphenyl)dodecane [3.93] also showed inhibition of 5-lipoxygenase from rat basophilic leukemia cells (RBL-1) with arachidonic acid as substrate.

The gingerol analogue, 3-hydroxy-1-(4-hydroxy-3-methoxyphenyl)dodecane [3.93],was tested on guinea pig submaxillary membrane for neurokinin-1 (NK-1) antagonist activity with tritium labelled [$^3$H]Substance P and found to have relatively potent inhibition of the binding of Substance P to NK-1 receptor.

Acute toxicity of the gingerol analogue, 3-hydroxy-1-(4-hydroxy-3-methoxyphenyl)dodecane [3.93] was evaluated on mice for 3 days and found, for intraperitoneal administration, to cause a slight decrease in spontaneous activity, response to touch and limb tone in mice. However, no toxicity was shown towards mice for dose by the oral route. The compound showed low toxicity towards brine shrimp. Brine shrimp toxicity for gingerols and gingerol analogues tested ranged from low to moderate.

Discussion of Results

We have reviewed evidence and preliminary work showing that gingerols and capsaicin, which are members of the vanilloid chemical family, may act by similar mechanisms in producing positive inotropic effects on guinea pig heart and vasorelaxation in rat mesenteric artery. However, it is unknown whether they act on the same receptors, on related receptor subtypes or on different but linked receptors. There is considerable information on the nature of capsaicin receptors, but nothing is known about the site of action of gingerols. In both groups of compounds the 4-hydroxy-3-methoxy (vanilloid) substitution is essential for biological activity. We showed that the side chain could be modified by changing the relationship between the keto and hydroxy substituent.

The vasorelaxant effect of gingerol analogue 3-hydroxy-1-(4-hydroxy-3-methoxyphenyl)dodecane [3.93] appears to be unrelated to release of cGRP, the major vasorelaxant peptide with other vasorelaxants studied. Operation of a novel vasorelaxant pathway is suggested by these results. The established action of capsaicin in anti-nociception, probably related to depletion of the neurotransmitter Substance P from sensory nerves, and hence tolerance of the relay of pain sensation via afferent nerve pathways to the central nervous system, indicates a role for capsaicin derivatives (including potentially 3-hydroxy-1-(4-hydroxy-3-methoxyphenyl)dodecane [3.93] and other derivatives) as candidate analgesic agents and for inhibition of neurogenic inflammation (Wrigglesworth et al, 1996). In addition, the gingerol analogues, as shown by 3-hydroxy-1-(4-hydroxy-3-methoxyphenyl)dodecane [3.93], may exert their antinociceptive activity by inhibition of Substance P from binding to NK-1 receptor.

A number of novel substances (gingerol analogues) have been found that are much more chemically stable than the gingerols which are relatively unstable under both chemical (Mustafa et al., 1993) and biological (Young-Joon, 1992, 1994) conditions, forming inactive substances. The β-hydroxycarbonyl function of the gingerols is vulnerable to oxidation or dehydration (Mustafa et al, 1993) to form inactive products. The gingerols are particularly prone to rapid dehydration under acidic conditions (Mustafa et al, 1993) such that even the pure substance is difficult to store for long periods. Simple oral dosing of the gingerols for medicinal action would not be possible due to the acidic environment of the stomach and upper intestinal tract. Chemical and biological instability is also likely to be a serious problem for intravenous doses.

Other useful bioactivities and properties have been reported for gingerols and related substances, for example, antipyretic, antihepatotoxic (Hikino et al, 1985) and antischistosomal activities (Young-Joon, 1992, 1994; Suekawa et al, 1984), antiulcer (Yamahara et al, 1992; Yoshikawa et al, 1992) and antioxidant activities (Aeschbach et al, 1994). The action of gingerols and chemically related substances in suppression of spontaneous calcium spikes and contraction in isolated portal veins of mice has also been reported (Kimura et al, 1988).

In work carried out in our laboratories, guinea pig atria organ bath tests did not give the predicted results, suggesting that the proposed mode of action of this class of compounds (Kobayashi et al., 1988) needs to be reinvestigated. A gingerol analogue 3-hydroxy-1-(4-hydroxy-3-methoxyphenyl)decanone [3.92], an isomer of [6]-gingerol), has potent stimulatory activity towards dog heart SR $Ca^{2+}$-ATPase (200% at 3 μM and 95% at 25 μM for the gingerol analogue [3.92]), whereas preliminary results from the guinea pig atria organ bath studies showed negative inotropic activity and negative chronotropic activity. In later studies positive inotropic activity was observed as a 50% increase on driven guinea pig left atria at 10 μM.

Positive inotropic and chronotropic activity were observed for other gingerol analogues [see Table 1]. 3-Hydroxy-1-(4-hydroxy-3-methoxyphenyl)decanone [3.92] showed 50% increase on guinea pig driven left atria at 10 μM and 3-hydroxy-1-(4-hydroxy-3-methoxyphenyl) dodecane [3.93] showed 50% increase at 1 μM followed by arrhythmia. Neither blocked ATP or $\alpha_1$-receptors in vas deferens. No effect was observed on nerve stimulation in atria.

3-Hydroxy-1-(4-hydroxy-3-methoxyphenyl)decanone [3.92] at up to 10 μM showed only a small effect on the rate of rise of $Na^+$-dependent action potential, amplitude of action potential, and duration of action potential (at 50% or 90% recovery).

Cardiotonic Substances of Interest

Of particular interest are gingerol analogues of novel structure showing cardiotonic activity (Table 1) i.e.

3-hydroxy-1-(4-hydroxy-3-methoxyphenyl)dodecan-5-one ([8]-inversegingerol) [3.90], 3-hydroxy-1-(4-hydroxy-3-methoxyphenyl)dodecanone [3.91], 3-hydroxy-1-(4-hydroxy-3-methoxyphenyl)decanone [3.92], 1-(4-hydroxy-3-methoxyphenyl)dodecan-3-ol [3.93].

Of potential interest is 3-hydroxy-1-(4-hydroxy-3-methoxyphenyl)dodecanone [3.91]. This substance is a homologue of the cardiotonic 3-hydroxy-1-(4-hydroxy-3-methoxyphenyl)decanone [3.92].

ATPase activities are a subject of this investigation. Filling of the SR stores by stimulation of SR $Ca^{2+}$,-ATPase may be of benefit in enhancing cardiac contractility whereas simultaneous stimulation of the PM $Ca^{2+}$-ATPase may aid in relaxation during diastole. Compounds of this class may be of considerable interest.

Our research includes mechanisms which directly control the level of intracellular calcium which is important for excitation-contraction coupling. There have been reports that [8]-gingerol, isolated from ginger, specifically activates sarcoplasmic reticulum (SR) $Ca^{2+}$-ATPase at low concentrations but inhibits the enzyme at high concentrations (Kobiyashi et al, 1987). [8]-Gingerol was also found to exhibit relatively potent cardiotonicity towards guinea pig atria.

This observation was confirmed by our laboratory for both [6]- and [8]-gingerol. Although the mechanism of the cardiotonic action has been reported to be the result of activation of SR $Ca^{2+}$-ATPase evidence for this is circumstantial or indirect, therefore the mechanism of action is uncertain. Evidence that the SR $Ca^{2+}$-ATPase may not be directly involved in the cardiotonic action comes from the observation of a very rapid dose-dependent response 15–20 seconds after addition of the gingerol to the guinea pig atria organ bath. A very rapid onset of action is unlikely to be due to activation of SR $Ca^{2+}$-ATPase which is located deep within the cell. Other evidence comes from studies of gingerol analogues where cardiotonic action does not correlate with activation of SR $Ca^{2+}$-ATPase and in some cases cardiotonic gingerol analogues showed inhibitory activity towards SR $Ca^{2+}$-ATPase.

The gingerol analogues may be useful for the treatment of heart failure through increase in strength of contraction of the heart. Also of particular interest with regard to cardiotonic activity of the gingerol analogues (and the gingerols) is the increase in relaxation of the guinea pig atria observed in the diastolic phase (observed as a decrease in the baseline tension after addition of the compound in the assay). This activity may be of use in the treatment of diastolic heart failure.

EXPERIMENTAL

I. Synthesis of Gingerols and Their Derivatives

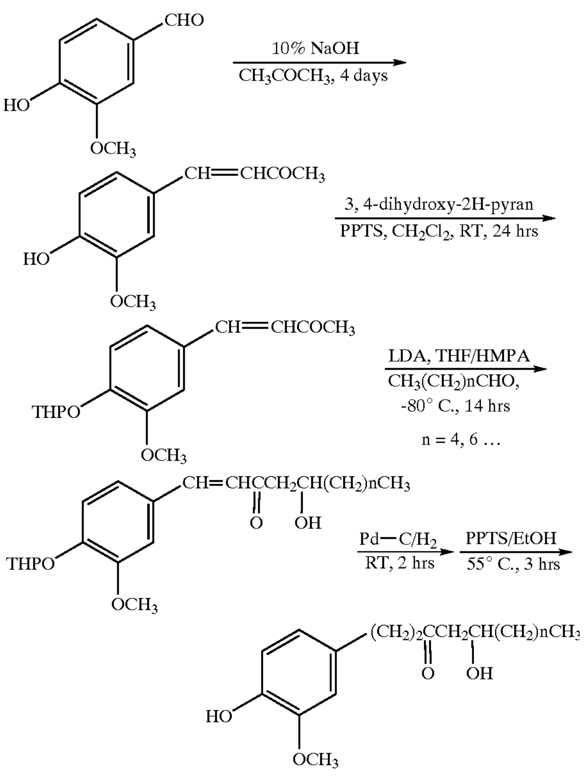

1. Preparation of Dehydrogingerone

To a solution of vanillin (5 g) in acetone (20 mL) was added 10% sodium hydroxide solution (20 mL). The reaction mixture was stirred at room temperature for 4 days (Normura, 1917). After acidification the product was extracted with EtOAc twice and washed with water. Evaporation of solvent left a dark brown liquid which on crystallisation from EtOAc-petroleum afforded the title compound (85%).

2. Preparation of Dehydrogingerone-THP (2)

A mixture of dehydrogingerone (5 g) and pyridinium p-toluene sulfonate (PPTS ) (0.1 g) in dichloromethane (20 mL) was stirred at room temperature for 24 hrs (Miyashita et al., 1977). After removal of solvent, the crude product was subjected to gradient chromatography to give a colourless solid (92%) which was sufficiently pure for the next reaction.

3. Preparation of 5-hydroxy-1-(4-hydroxy-3-methoxyphenyl)decan-3-one ([6]-gingerol)

To a stirred solution of LDA (0.15 moles, prepared by treating diisopropylamine with 2.5 M butyllithium in hexane), under $N_2$, in THF (4 mL) and HMPA (1 mL) at −78° C. was added dropwise a solution of 2 (0.1 moles) in THF (2 mL). After stirring for 20 mins, an appropriate aldehyde (0.12 moles) in THF (1 mL) was added dropwise. The reaction mixture was stirred at −78° C. for overnight, extracted with $Et_2O$ twice, washed with diluted HCl, then with water. Evaporation of solvent left a yellowish liquid which was subjected to gradient chromatography to give the dehydrogingerol-THP. The product subsequently underwent hydrogenation at room conditions with hydrogen and Pd—C, and deprotection of the THP ether, using PPTS in ethanol, to afford a light yellow liquid which was purified by gradient chromatography to give a colourless liquid. Yield 60%.

$^{1}$H-NMR: δ6.81 (1H, d, J=8 Hz), 6.67 (2H, m), 4.02 (1H, m), 3.86 (3H, s, $OCH_3$), 2.77 (4H, m), 2.52 (2H, m), 1.28 (8H, m), 0.88 (3H, t, b). $^{13}$C-NMR: δ14.03, 22.59, 25.13, 29.27, 31.72, 36.41, 45.43, 49.34, 55.86, 67.66, 110.97, 114.38, 120.71, 132.62, 143.95, 146.43.

CI-MS $\{M+1\}^+$ 295 (15), $\{M+1-H_2O\}^+$ 277 (100), $\{C_{10}H_{11}O_3\}^+$ 179 (30), $\{C_8H_9O_2\}^+$ 137 (35).

A similar procedure was applied to the synthesis of other gingerol derivatives.

5-hydroxy-1-(4-hydroxy-3-methoxyphenyl)dodecan-1-ene-3-one ([8]-dehydrogingerol): mp. $^{1}$-NNR: δ7.56 (1H, d, J=15 Hz), 7.11 (1H, dd, J=8, 2 Hz), 7.06 (1H, d, J=2 Hz), 6.94 (1H, d, J=8 Hz), 6.58 (1H, d, J=15 Hz), 4.02 (1H, m), 3.87 (3H, s, $OCH_3$), 2.78 (2H, m), 1.51 (2H, m), 1.29 (10H, m), 0.89 (3H, t, b).

5-hydroxy-1-(4-hydroxy-3-methoxyphenyl)dodecan-3-one ([8]-gingerol): Liquid.

$^{1}$H-NMR: δ6.81 (1H, d, J=8 Hz), 6.67 (2H, m), 4.02 (1H, m), 3.86 (3H, s, $OCH_3$), 2.77 (4H, m), 2.52 (2H, m), 1.28 (12H, m), 0.88 (3H, t, b). $^{13}$C-NMR: δ14.03, 22.64, 25.45, 29.27, 29.24, 29.28, 29.49, 31.79, 36.45, 45.43, 49.34, 55.86, 67.66, 110.97, 114.38, 120.71, 132.62, 143.95, 146.43.

CI-MS: $\{M+1\}^+$ 323 (15), $\{M+1-H_2O\}^+$ 305 (100), $\{C_{10}H_{11}O_3\}^+$ 179 (20), $\{C_8H_9O_2\}^+$ 137 (20).

5-hydroxy-1-(2-hydroxy-3-methoxyphenyl)dodecan-3-one: ([8]-o-gingerol prepared using o-vanillin instead of vanillin as starting material).

Liquid. $^{1}$H-NMR: δ6.75 (3H, m), 4.02 (1H, m), 3.86 (3H, s, $OCH_3$), 2.77 (4H, m), 2.52 (2H, m), 1.28 (12H, m), 0.88 (3H, t, b). $^{13}$C-NMR: δ14.03, 22.70, 25.51, 29.29, 29.56, 31.85, 36.45, 43.41, 49.08, 49.99, 56.02, 67.66, 108.92, 119.55, 122.34, 126.57, 143.56, 146.54.

CI-MS: $\{M+1-H_2O\}^+$ 305 (30), $\{C_{10}H_9O_3\}^+$ 177 (100).

EI-MS: {M} 322 (5), $\{M-H_2O\}$ 304 (20), $\{C_{12}H_{13}O_3\}$ 205 (30), $\{C_{12}H_{18}O_2\}$ 194 (20), $\{C_{10}H_{10}O_3\}$ 178 (25), $\{C_8H_9O_2\}$ 137 (60), $\{C_5H_5O\}$ 81 (25), $\{C_4H_9\}$ 69 (60), $\{C_4H_9\}$ 57 (40), $\{C_3H_5\}$ 41 (100).

HRMS: $C_{19}H_{30}O_4$ Calculated 322.214, Found 322.214.

5-hydroxy-1-(4-hydroxy-3-methoxyphenyl)dodecan-3-one: ([8]-isogingerol prepared using isovanillin instead of vanillin as starting material).

Liquid. $^{1}$H-NMR: δ6.75 (2H, m), 6.64 (1H, dd, J=8, 2 Hz), 4.02 (1H, m), 3.86 (3H, s, $OCH_3$), 2.77 (4H, m), 2.52 (2H, m), 1.26 (12H, m), 0.88 (3H, t, b). $^{13}$C-NMR: δ14.15, 22.70, 25.51, 28.99, 29.29, 29.55, 31.85, 36.48, 45.21, 49.31, 56.04, 67.68, 110.73, 114.44, 119.68, 134.01, 145.03, 145.61.

CI-MS: $\{M+1\}^+$ 323 (10), $\{M+1-H_2O\}^+$ 305 (100), $\{C_{10}H_{11}O_3\}^+$ 179 (40), $\{C_8H_9O_2\}^+$ 137 (18).

5-hydroxy-1-(4-hydroxyphenyl)decan-3-one: ([6]-demethoxygingerol prepared using 4-hydroxybenzaldehyde instead of vanillin as starting material).

mp 43–45° C. $^{1}$H-NMR. δ7.02 (2H, d, J=8 Hz), 6.73 (2H, d, J=8 Hz), 4.03 (1H, m), 2.77 (4H, m), 2.52 (2H, m), 1.28 (8H, m), 0.88 (3H, t, b). $^{13}$C-NMR: δ14.07, 22.63, 25.13, 28.73, 31.72, 36.41, 45.37, 49.29, 67.81, 115.41, 129.42 (2C), 132.70 (2C), 154.11.

CI-MS: $\{M+1-H_2O\}^+$ 247 (30), $\{C_{11}H_{13}O_2\}^+$ 177 (100).

EI-MS: {M} 264 (10), {M-$H_2O$} 246 (20), {$C_{11}H_{11}O_2$} 175 (80), {$C_8H_8O$} 120 (40), {$C_7H_7O$} 107 (100), {$C_4H_7$} 55 (100), {$C_3H_5$} 41 (55).

HRMS: $C_{16}H_{24}O_3$ Calculated 264.173, Found 264.172.

5-hydroxy-1-(4-hydroxyphenyl)dodecan-3-one: ([8]-demethoxygingerol, preparation similar to that of [6]-demethoxygingerol).

mp 81–82° C. $^1$H-NMR: δ6.81 (2H, d, J=8 Hz), 6.67 (2H, d, J=8 Hz), 4.02 (1H, m), 3.86 (3H, s, $OCH_3$), 2.77 (4H, m), 2.52 (2H, m), 1.28 (12H, m), 0.88 (3H, t, b). $^{13}$C-NMR: δ14.03, 22.64, 25.45, 29.27, 29.24, 29.28, 29.49, 31.79, 36.45, 45.43, 49.34, 55.86, 67.66, 110.97, 114.38, 120.71, 132.62, 143.95, 146.43.

CI-MS: $\{M+1-H_2O\}^+$ 275 (60), $\{C_9H_9O_2\}^+$ 149 (25), $\{C_7H_7O\}^+$ 107 (100).

EI-MS: {M} 292 (18), {M-$H_2O$} 274 (18), {$C_{11}H_{11}O_2$} 175 (65), {$C_9H_9O_2$} 149 (20), {$C_8H_8O$} 120 (60), {$C_7H_7O$} 107 (100), {$C_5H_9$} 69 (30), {$C_4H_7$} 55 (60), {$C_3H_7$} 43 (90).

HRMS: $C_{18}H_{28}O_3$ Calculated 292.204, Found 292.205.

5-hydroxy-1-(3,4-methylenedioxyphenyl)dodecan-3-one: [prepared using piperonal instead of vanillin as starting material]

mp 48–50° C. $^1$H-NMR: δ6.72 (1H, d, J=8 Hz), 6.66 (1H, d, J=2 Hz), 6.62 (1H, dd, J=8, 2 Hz), 5.92 (2H, s, $OCH_2O$), 4.03 (1H, m), 2.75 (4H, m), 2.53 (2H, m), 1.27 (12H, m), 0.88 (3H, t, b). $^{13}$C-NMR: δ14.14, 22.69, 25.50, 29.28, 29.31, 29.54, 31.84, 36.51, 45.35, 49.36, 67.68, 100.89, 108.32, 108.80, 121.08, 134.55, 145.92, 147.70.

CI-MS: $\{M+1-H_2O\}^+$ 303 (50), $\{C_{11}H_{13}O_3\}^+$ 193 (25), $\{C_8H_7O_2\}^+$ 135 (100), $\{C_8H_{15}\}^+$ 111 (50).

EI-MS: {M} 320 (40), {M-$H_2O$} 302 (60), {$C_{12}H_{11}O_3$} 203 (70), {$C_9H_8O_2$} 148 (40), {$C_8H_7O_2$} 135 (100), {$C_5H_9$} 69 (30), {$C_4H_6$} 54 (50), {$C_3H_6$} 42 (45).

5,12-dihydroxy-1,16-bis(4-hydroxy-3-methoxyphenyl)-hexa-decane-3,14-dione:

[prepared using 1,8-octandial instead of aliphatic aldehyde as starting material]

mp 65–68° C. $^1$H-NMR: ($CD_3COCD_3$) δ6.82 (2H, d, J=2 Hz), 6.71 (2H, d, J=8 Hz), 6.65 (2H, dd, J=8, 2 Hz), 4.01 (2H, m), 3.81 (6H, S, $OCH_3$), 2.77 (8H, m), 2.52 (4H, m), 1.30 (12H, m). $^{13}$C-NMR: ($CD_3COCD_3$) δ26.18 (2C), 38.1 (2C), 38.14 (2C), 45.86 (2C), 50.89 (2C), 50.94 (2C), 56.14 (2C), 68.15 (1C), 68.28 (1C), 112.72 (2C), 115.51 (2C), 115.6 (2C), 121.39 (2C), 133.61 (2C).

CI-MS: $\{M+1\}^{30}$ 531 (100), $(M+1-H_2O)^+$ 513 (70), $\{M+1-2H_2O\}^+$ 495 (15), $\{C_{19}H_{27}O_4\}^+$ 319 (50), $\{C_{10}H_{11}O_3\}^+$ 179 (10), $\{C_8H_9O_2\}^+$ 137 (80).

EI-MS: $C_{12}H_{13}O_3$} 205 (10), {$C_{11}H_{14}O_3$} 194 (15), {$C_9H_{10}O_2$} 150 (15), {$C_8H_9O_2$} 137 (100), {$C_4H_7$} 55 (25), {$C_3H_7$} 43 (80).

II. Synthesis of 3-hydroxy-1-(4-hydroxy-3-methoxyphenyl)dodecan-5-one

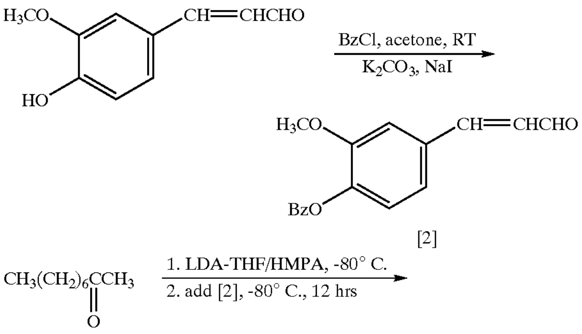

[2]

-continued

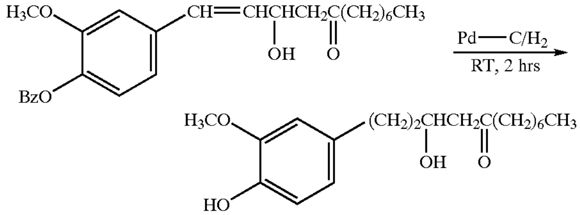

1. Preparation of 4-benzyloxy-3-methoxycinnamaldehyde

4-Hydroxy-3-methoxycinnamaldehyde (0.6 g) was added to the mixture of benzyl chloride (1 mL), $K_2CO_3$ (1 g), and NaI (1 g) in acetone (20 mL). The resulting mixture was stirred at room temperature for 24 hrs. The solid were removed by filtration and washed with acetone. After evaporation of solvent, the crude product was purified by gradient chromatography to give a yellowish solid. Yield 85%.

2. Preparation of 3-hydroxy-1-(4-hydroxy-3-methoxyphenyl)dodecan-5-one

To a stirred solution of LDA (0.15 moles, prepared by treating diisopropylamine with 2.5 M butyllithium in hexane), under $N_2$, in THF (4 mL) and HMPA (1 mL) at −78° C., was added dropwise a solution of 2-nonanone (0.1 moles) in THF (1 mL). After stirring for 20 mins, 4-benzyloxy-3-methoxycinnamaldehyde (0.11 moles) in THF (2 mL) was added dropwise. The reaction mixture was stirred at −78° C. overnight, then quenched with dilute HCl, extracted with $Et_2O$ twice. Evaporation of solvent left a yellowish liquid which was subjected to gradient chromatography to give a yellow solid. The product subsequently underwent hydrogenation at room temperature and atmospheric pressure with hydrogen and Pd—C for 2 hrs to afford the title compound which was then purified by gradient chromatography to give a colourless solid. Yield 60%. mp 42–43° C. $^1$H-NMR: δ6.84 (1H, d, J=8 Hz), 6.72 (1H, d, J=2 Hz), 6.70 (1H, dd, J=8, 2 Hz), 4.05 (1H, m), 3.88 (3H, s, $OCH_3$), 2.60 (4H, m), 2.41 (2H, t, J=6 Hz), 1.60 (4H, m), 1.27 (8H, m), 0.88 (3H, t, b). $^{13}$C-NMR: δ14.11, 22.64, 23.67, 29.08, 29.16, 31.50, 31.69, 38.41, 43.72, 48.93, 55.92, 66.92, 111.10, 114.26, 120.95, 133.83, 143.73, 146.41.

CI-MS: $\{M+1\}^+$ 323 (100), $\{M+1-H_2O\}^+$ 305 (60), $\{C_{10}H_{11}O_2\}^+$ 163 (20), $\{C_8H_9O_2\}^+$ 137 (40), $\{C_8H_{15}O\}^+$ 127 (30).

EI-MS: {M} 322 (80), {M-$H_2O$} 304 (50), {$C_{12}H_{13}O_3$} 205 (10), {$C_{11}H_{13}O_2$} 177 (18), {$C_{10}H_{11}O_2$} 163 (25), {$C_9H_{10}O_2$} 150 (20), {$C_8H_9O_2$} 137 (100), {$C_8H_{15}O$} 127 (25).

HRMS: $C_{19}H_{30}O_4$ Calculated 322.214, Found 322.215.

III. Synthesis of 3-hydroxy-1-(4-hydroxy-3-methoxyphenyl)decanone

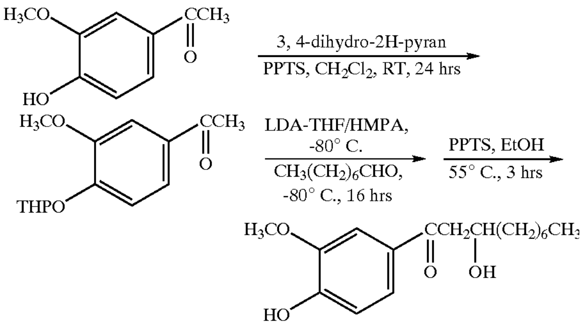

To a stirred solution of LDA (0.15 moles, prepared by treating diisopropylamine with 2.5 M butyllithium in hexane), under $N_2$, in THF at −78° C was added dropwise a solution of acetovanillone-THP (0.1 moles), which was prepared as described for dehydrogingerone-THP, in THF (4 mL). After stirring for 20 mins, octanal (0.12 moles) in THF (2 mL) was added dropwise. The reaction mixture was stirred at −78° C. overnight, then quenched with dilute HCl and extracted with ether twice. Evaporation of solvent left a yellowish liquid which was subjected to gradient chromatography to give the product. This was subsequently deprotected using PPTS in ethanol, to afford a light yellow liquid which was again subjected to gradient chromatography to give the title compound as a colourless solid. Yield 70–80%. mp 77–78° C. $^1$H-NMR: δ7.53 (2H, m), 6.94 (1H, d, J=8 Hz), 4.19 (1H, m), 3.96 (3H, s, $OCH_3$), 3.10 (2H, m), 1.30 (12H, m), 0.88 (3H, t, b). $^{13}$C-NMR: δ14.15, 22.71, 25.66, 29.33, 29.64, 31.88, 36.62, 44.41, 56.13, 68.07, 109.63, 113.94, 123.74, 129.84, 146.73, 150.83, 199.64.

EI-MS: {M} 294 (10), {M−$H_2O$} 276 (10), {$C_{10}H_{11}O_4$} 195 (15), {$C_9H_{10}O_3$} 166 (40), {$C_8H_7O_3$} 151 (100), {$C_7H_7O_2$} 123 (10).

HRMS: $C_{17}H_{26}O_4$ Calculated 294.183, Found 294.185.

A similar procedure to the above was applied to synthesise the following compound.

3-hydroxy-1-(4-hydroxy-1-methoxyphenyl)dodecanone: mp 74–76° C. $^1$H-NMR: δ7.53 (2H, m), 6.94 (1H, d, J=8 Hz), 4.19 (1H, m), 3.96 (3H, s, $OCH_3$), 3.10 (2H, m), 1.30 (16H, m), 0.88 (3H, t, b). $^{13}$C-NMR: δ14.15, 22.71, 25.66, 29.33, 29.64, 29.67, 29.74, 31.85, 36.62, 44.41, 56.13, 68.07, 109.63, 113.94, 123.74, 129.84, 146.73, 150.84.

CI-MS: $\{M+1\}^+$ 323 (100), $\{M+1-H_2O\}^+$ 305 (25), $\{C_8H_7O_3\}^+$ 151 (20).

MS-EI: {M} 322 (20), {M−$H_2O$} 304 (15), {M −47} 279 (15), {$C_{10}H_{11}O_4$} 195 (25), {$C_9H_{10}O_3$} 166 (40), {$C_8H_7O_3$} 151 (100), {$C_7H_7O_2$} 123 (10).

HRMS: $C_{19}H_{30}O_4$ Calculated 322.214, Found 322.213.

IV. Synthesis of 1-(4-hydroxy-3-methoxyphenyl) dodecan-3-ol

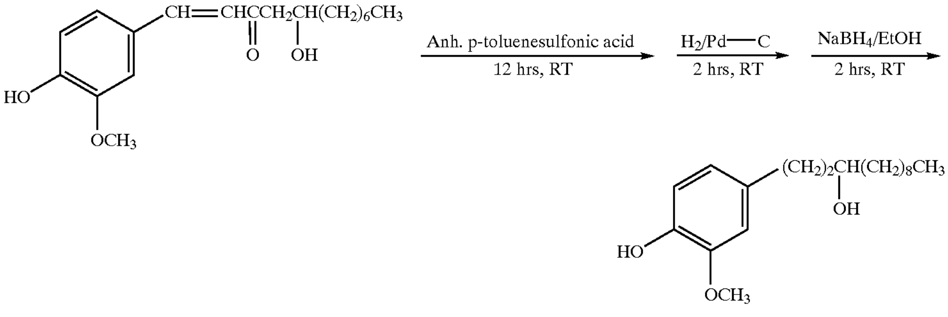

To a solution of 8-dehydrogingerol (0.1 g) in dichloromethane (20 mL) was added anhydrous p-toluenesulfonic acid (0.05 g ). The mixture was stirred at room temperature overnight. Evaporation of solvent left a dark brown liquid which subsequently was hydrogenated with $H_2$/Pd—C, then reduced with sodium borohydride in ethanol to produce the title compound in quantitative yield.

mp 66—68° C. $^1$H-NMR: δ6.84 (1H, d, J=8 Hz), 6.72 (1H, d, J=2 Hz), 6.69 (1H, dd, J=8, 2 Hz), 3.89 (3H, s, $OCH_3$), 3.63 (1H, m), 2.70 (2H, m), 1.74 (2H, m), 1.47 (2H, m), 1.27 (14H, m), 0.89 (3H, t, b). $^{13}$C-NMR: δ14.17, 22.73, 25.68, 29.37, 29.61, 29.67, 29,74, 31.85, 31.94, 37.70, 39.43, 55.91, 71.49, 111.00, 114.26, 120.91, 134.17, 143.68, 146.41.

CI-MS: $\{M+1\}^+$ 309 (10), $\{M+1-H_2O\}^+$ 291 (100), $\{C_8H_9O_2\}^+$ 137 (55).

EI-MS: {M} 308 (65), {M−$H_2O$} 290 (25), {$C_9H_{10}O_2$} 150 (25), {$C_8H_{10}O_2$} 138 (100), {$C_7H_8O_2$} 124 (12), {$C_4H_7$} 43 (55).

HRMS: $C_{19}H_{32}O_3$ Calculated 308.235, Found 308.234.

1-(4-hydroxy-3-methoxyphenyl)dodecane-1,4-diene-3-one: (isolated as an intermediate product). Liquid. $^1$H-NMR: δ7.59 (1H, d, J=15 Hz), 7.14 (1H, dd, J=8, 2 Hz), 7.08 (1H, d, J=2 Hz), 7.02 (1H, m), 6.93 (1H, d, J=8 Hz), 6.82 (1H, d, J=15 Hz), 6.45 (1H, m), 3.94 (3H, s, $OCH_3$), 2.29 (2H, m), 1.51 (2H, m), 1.31 (8H, m), 0.88 (3H, t, b). $^{13}$C-NMR: δ14.14, 22.69, 28.27, 29.14, 29.26, 31.8, 32.78, 56.01, 109.74, 114.88, 122.83, 123.34, 127.41, 129.08, 143.37, 146.88, 148.08, 148.21, 189.35.

EI-MS: {M} 302 (100), {M−17} 285 (15), {M−31} 271 (10), {$C_{14}H_{15}O_3$} 231 (10), {$C_{13}H_{13}O_3$} 217 (100), {$C_{12}H_{12}O_3$} 204 (30), {$C_{12}H_9O_2$} 185 (20), {$C_{10}H_9O_3$} 177 (40), {145 (30), {$C_8H_9O_2$} 137 (60), {117 (20), 89 (20), {49 (15), {$C_4H_7$} 55 (60), {$C_3H_7$} 43 (90).

HRMS: $C_{19}H_{26}O_3$ Calculated 302.188, Found 302.189.

A similar procedure to the above was applied to prepare its homologue.

1-(4-hydroxy-3-methoxyphenyl)dodecane-5-ol: mp 54–55° C. $^1$H-NMR: δ6.82 (1H, d, J=8 Hz), 6.67 (2H, m), 3.88 (3H, s, $OCH_3$), 3.60 (1H, m), 2.56 (2H, t, J=6 Hz), 1.65 (2H, m), 1.35 (16H, m), 0.88 (3H, t, b). $^{13}$C-NMR: δ14.16, 22.72, 25.36, 25.71, 29.35, 29.72, 31.89, 31.91, 35.67, 37.35, 37.58, 55.90, 71.99, 111.01, 114.20, 120.91, 134.64, 143.59, 146.37.

EI-MS: {M} 308 (100), {M−$H_2O$} 290 (50), {$C_8H_9O_2$} 137 (75), }$C_5H_9$} 69 (10), {$C_4H_7$} 55 (25).

HRMS: $C_{19}H_{32}O_3$ Calculated 308.235, Found 308.236.

V. Synthesis of 1-(4-hydroxy-3-methoxyphenyl) dodecane-3,5-diol ([8]-gingerdiol)

8-gingerol

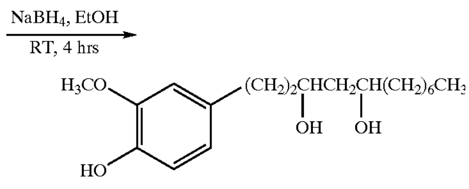

To a solution of [8]-gingerol (0.1 g) in EtOH (15 mL) was added dropwise a solution of $NaBH_4$ (0.02 g in 1 mL $H_2O$). The mixture was stirred at room temperature for 3 hrs. After acidification, EtOAc was added and organic layer was washed with water twice. Evaporation of solvent left a white solid which was purified by gradient chromatography to afford the title compound as a colourless liquid in quantitative yield.

$^1$H-NMR: δ6.82 (1H, d, J=8 Hz), 6.71 (1H, d, J=2 Hz), 6.67 (1H, dd, J=8, 2 Hz), 3.97 (2H, m), 3.86 (3H, s, $OCH_3$), 2.65 (2H, m), 1.81 (2H, m), 1.69 (14H, m), 0.87 (3H, t, b).

$^{13}$C-NMR: δ14.13, 22.69, 24.99, 29.29, 29.34, 29.55, 30.90, 31.84, 37.22, 39.22, 55.91, 71.77, 72.74, 111.20, 114.34, 120.98, 133.73, 143.74, 146.47.

CI-MS: $\{M+1\}^+$ 325 (25), $\{M+1-H_2O\}^+$ 307 (45), $\{M+1-2H_2O\}^+$ 289 (100), $\{C_{10}H_{11}O_2\}^+$ 163 (20), $\{C_8H_9O_2\}^+$ 137 (50).

Preparation of 3-methyl-1-(4-hydroxy-3-methoxyphenyl)-undecan-3-ol

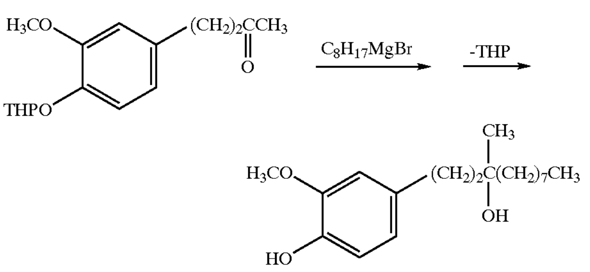

To a Grignard solution of octylmagnesiumbromide, prepared from Mg (0.05 g) and 1-bromooctane (0.36 g), in THF (5 ml) under $N_2$ was added gingerone-THP (0.5 g) in THF (5 ml) which was prepared as described for dehydrogingerone-THP above. The mixture was stirred at room temperature overnight. The product was extracted with diethyl ether (50 ml), washed with brine solution and purified by column chromatography to give a colourless liquid (yield 60%).

$^1$-NMR: δ6.82 (1H, dd, J=8, 2 Hz), 6.7(2H, m), 5.47 (1H, s), 3.88 (3H, s), 2.6 (2H, m), 1.73 (2H, m), 1.5 (2H, m), 1.2–13 (16H, m), 0.88 (3H, t, b). $^{13}$C-NMR: δ14.17, 22.73, 24.03, 26.93, 29.34, 29.66, 30.05, 30.28, 31.94, 42.13, 43.98, 55.91, 72.67, 110.93, 114.23, 120.81, 134.57, 143.55, 146.36.

CI-MS: $\{M+1\}^+$ 291, $\{C_8H_9O_2\}^+$ 137; EI-MS: {M} 290.

Similar procedure was used to synthesise 3-methyl-1-(4-hydroxy-3-methoxyphenyl)tridecan-3-ol.

$^1$H-NMR: δ6.82 (1H, dd, J=8, 2 Hz), 6.7(2H, m), 5.49 (1H, s), 3.88 (3H, s), 2.6 (2H, m), 1.73 (2H, m), 1.5 (2H, m), 1.2–13 (20H, m), 0.88 (3H, t, b). $^{13}$C-NMR: δ14.18, 22.74, 24.04, 26.99, 29.4, 29.68 (3C), 30.06, 30.28, 31.96, 42.18, 44.02, 55.91, 72.8, 110.93, 114.3, 120.81, 134.59, 143.65, 146.43.

CI-MS: $\{M+1\}^+$ 319, $\{C_8H_9O_2\}^+$137; EI-MS: $\{M\}^+$ 318.

Preparation of 2-hydroxy-1-(4-hydroxy-3-methoxyphenyl)undecan-1-one

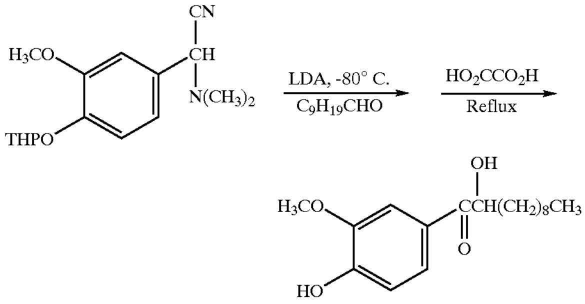

1. Preparation of 1-(N,N-dimethylamino)-1-(4-hydroxy-3-methoxyphenyl)acetonitrile The synthesis followed a published method (Hauser et al., 1960). Briefly, to a stirred solution of $NaHSO_3$ (0.7 g) in water (4 ml) was added vanillin-THP (1.4 g), prepared as described for dehydrogingerone-THP above, in MeOH (20 ml), followed by the addition of anhydrous dimethylamine (0.5 g) in cold MeOH (30 ml). The mixture was cooled prior to the addition of an aqueous solution of NaCN (0.5 g, 2 ml). After 24 hrs stirring at room temperature, the mixture was extracted with $Et_2O$ (50 ml), washed with water (2×20 ml), and evaporated to give a colourless liquid (yield >90%) which was sufficiently pure for the next reaction.

2. Preparation of 2-hydroxy-1-(4-hydroxy-3-methoxyphenyl)undecan-1-one

Under a $N_2$ atmosphere diisopropylamine (0.6 mL) dissolved in dry THF (10 mL) was treated with n-butyllithium (2.5 M, 2 mL) and stirred for 30 min at −80° C., followed by the addition of a solution of 1-(N,N-dimethylamino)-1-(4-hydroxy-3-methoxyphenyl)acetonitrile (0.8 g), which was prepared as described above, in THF (2 ml). The mixture was then stirred at −80° C. for 15 mins and at 0° C. for 2 hr. To this mixture was cooled to −80° C. and then a solution of decyl aldehyde (0.25 g) in THF (2 mL) was added dropwise. After 2 hrs stirring at −80° C., the mixture was extracted with $Et_2O$ (50 ml), washed with brine solution (20 ml) and evaporated to give a liquid which was purified by column chromatography to afford a colourless liquid (yield 60%).

mp 78–80° C.; $^1$H-NMR: δ7.53 (1H, d, J=2 Hz), 7.45 (1H, dd, J=8, 2 Hz), 6.96 (1H, d, J=8 Hz), 5.02 (1H, m), 3.97 (3H, s), 3.7 (1H, m), 1.84 (1H, m), 1.5–1.6 (3H, m), 1.23 (12H, m), 0.86 (3H, t, b). $^{13}$C-NMR: δ14.16, 22.71, 24.98, 29.33, 29.44, 29.51, 29.54, 31.91, 36.61, 56.18, 72.67, 110.36, 114.11, 123.88, 126.35, 146.91, 151.13.

CI-MS: $\{M+1\}^+$ 309; EI-MS: {M} 308.

Similar procedure was used to synthesise 1-hydroxy-1-(4-hydroxy-3-methoxyphenyl)undecan-2-one where 1-(N, N-dimethylamino)-1-decylcyanide was formed instead and reacted with vanillin-THP.

mp 51–53° C. $^1$H-NMR: δ6.91 (1H, d, J=8 Hz), 6.85 (1H, dd, J=8, 2 Hz), 6.72 (1H, d, J=2 Hz), 5.7 (1H, s), 5.0 (1H, d, J=4 Hz), 4.32 (1H, d, J=4 Hz), 3.87 (3H, s), 2.33 (2H, m), 1.5 (2H, m), 1.21 (12H, m), 0.86 (3H, t, b). $^{13}$C-NMR: δ14.14, 22.69, 23.78, 29.04, 29.25 (2C), 29.39, 31.88, 37.78, 56, 79.44, 109.06, 114.64, 121.23, 130, 146.1, 147.07.

CI-MS: $\{M+1\}^+$ 309; EI-MS: {M} 308.

Separation of Enantiomers of 1-(4-hydroxy-3-mothoxyphenyl)dodecan-3-ol

1. Preparation of endo-(−)- and (+)-1,4,5,6,7,7-hexachlorobicyclo[2.2.1]hept-5-ene-2-carboxylic acid (HCA). The synthesis followed a published method (Duke and Wells, 1987) in which the diastereomeric esters of HCA were formed using 2,3-O-isopropylidene-D(+)-ribono-1,4-lactone and subsequently separated by repeated fractional crystallisation from hexane/ethyl acetate to give colourless solids. The diastereomeric esters of HCA was hydrolysed to give endo-(−)- and (+)-HCA, respectively.

2. Preparation of diastereomeric esters of 1-(4-hydroxy-3-methoxyphenyl)dodecan-3-ol. endo-(+)-HCA (0.34 g) was refluxed with $SOCl_2$ (10 ml) for 1.5 hrs and the excess reagent was removed under vacuum. To the residue in THF (5 ml) was added a solution of 1-(4-hydroxy-3-methoxyphenyl)dodecan-3-ol (0.1 g) in dry THF (5 ml) and then p-dimethylaminopyridine (0.16 g) in THF (5 ml) was added slowly to the solution. A colourless solid was formed and the mixture was left standing for 3 hrs, then filtered, washed with THF and evaporated to give a colourless liquid. Two diastereomeric esters were separated by column chromatography, then hydrolysed to give, respectively, the two enantiomers of 1-(4-hydroxy-3-methoxyphenyl)dodecan-3-ol in quantitative yield.

Diastereomer-1 of 1-(4-hydroxy-3-methoxyphenyl)dodecan-3-ol $^1$H-NMR: δ6.95 (1H, d, J=8 Hz), 6.78 (2H, m), 4.97 (1H, m), 3.94 (1H, m), 3.8 (3H, s), 3.62 (1H, m), 2.5–2.85 (6H, m), 1.89 (2H, m), 1.56 (2H, m), 1.25 (14H, m), 0.88 (3H, t, b).

Diastereomer-2 of 1-(4-hydroxy-3-methoxyphenyl)dodecan-3-ol $^1$H-NMR: δ6.96 (1H, d, J=8 Hz), 6.75 (2H, m), 4.95 (1H, m), 3.94 (1H, m), 3.8 (3H, s), 3.47 (1H, m), 2.49–2.85 (6H, m), 1.9 (2H, m), 1.56 (2H, m), 1.26 (14H, m), 0.88 (3H, t, b).

The exact configuration of each enantiomer has not yet been determined. They are therefore named as enantiomer-1 (less polar) and 2 (more polar) according to the polarity of their diastereomeric esters on normal phase silica gel chromatography.

enantiomer-1 of 1-(4-hydroxy-3-methoxyphenyl)dodecan-3-ol:

mp 53–56° C. $^1$H-NMR: δ6.82 (1H, dd, J=8,2 Hz), 6.70 (2H, m), 3.87 (3H, s), 3.62 (1H, m), 2.5–2.8 (2H, m), 1.74 (2H, m), 1.46 (2H, m), 1.26 (14H, m), 0.87 (3H, t, b). $^{13}$C-NMR: δ14.16, 22.72, 25.67, 29.36, 29.6, 29.66, 29.73, 31.83, 31.94, 37.68, 39.41, 55.91, 71.5, 111.02, 114.28, 120.92, 134.17, 143.7, 146.43.

enantiomer-1 of 1-(4-hydroxy-3-methoxyphenyl)dodecan-3-ol:

mp 53–56° C. $^1$H-NMR: δ6.82 (1H, dd, J=8,2 Hz), 6.70 (2H, m), 3.87 (3H, s), 3.62 (1H, m), 2.5–2.8 (2H, m), 1.74 (2H, m), 1.46 (2H, m), 1.26 (14H, m), 0.87 (3H, t, b). $^{13}$C-NMR: δ14.16, 22.72, 25.67, 29.36, 29.6, 29.67, 29.73, 31.84, 31.94, 37.7, 39.43, 55.91, 71.5, 111, 114.26, 120.92, 134.18, 143.69, 146.42.

Synthesis of 2-hydroxy-1-(3,4-dimethoxyphenyl)dodecan-3-one

Preparation of 2-(3,4-dimethoxyphenyl)ethanol

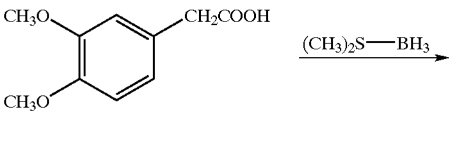

-continued

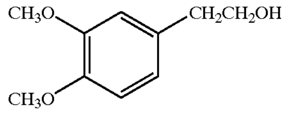

To a solution of 3,4-dimethoxyphenylacetic acid (2 g) in anhydrous THF (40 ml) at 0° C. under $N_2$ was added dropwise borane-methyl sulfide complex (10 M, 1.5 ml). The mixture was stirred at room temperature for further 4 hrs. Cold water (5 ml) was added to destroy any excess of borane followed by the addition of $H_2SO_4$ (1 M, 50 ml). The mixture was extracted three time with ethyl acetate (50 ml). The organic layer was separated and evaporated off to give a colourless liquid which was then purified by column chromatography to afford a colourless solid in quantitative yield.

$^1$H-NMR: δ6.76–6.82 (3H, m), 3.87 (8H, m), 2.82 (2H, t, J=6 Hz).

Preparation of 3,4-dimethoxyphenyl acetal

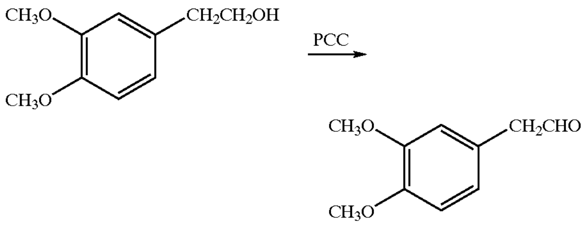

To a stirred suspension of pyridinium chlorochromate (2.5 g) in $CH_2Cl_2$ (40 ml) at room temperature was added a solution of 2-(3,4-dimethoxyphenyl)ethanol (2 g) in $CH_2Cl_2$ (10 ml) . The mixture was stirred at room temperature for further 30 min, then filtered through florisil. The solvent was evaporated off to give a liquid which was purified from column chromatography to afford a colourless liquid. Yield 40 %. $^1$H-NMR: δ9.73 (1H, t, J=2 Hz), 6.86 (1H, d, J=8 Hz), 6.77 (1H, dd, J=8, 2 Hz), 6.71 (1H, d, J=2 Hz), 3.88 (6H, s), 3.63 (2H, d, J=2 Hz).

Preparation of 2-hydroxy-1-(3,4-dimethoxyphenyl)dodecan-3-one

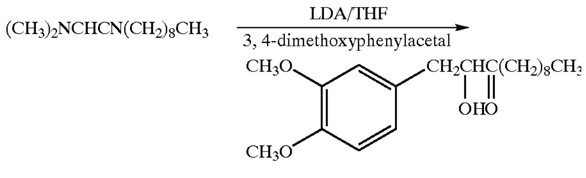

To a solution of diisopropylamine (0.4 mL) in anhydrous THF (10 mL) at −80° C., under $N_2$ was added dropwise n-butyllithium (2.5 M, 1.5 mL). The mixture was stirred on ice for 30 min, then cooled to −80° C. prior addition of the solution 1-(N,N-dimethylamino)-1-decylcyanide (0.36 g), which was prepared as described in the synthesis of 2-hydroxy-1-(4-hydroxy-3-methoxyphenyl)undecan-1-one (page 39), in THF (5 mL). The reaction mixture was stirred at −80° C. for 15 mins and at 0° C. for further 3 hr. To this mixture cooled at −80° C. was added dropwise a solution of 3,4-dimethoxyphenylacetal (0.4 g) in THF (5 mL). After 2 hrs stirring at −80° C., the mixture was extracted twice with $Et_2O$ (50 ml), washed with 1 M HCl (50 ml), then water (50 ml). The organic layer was evaporated to give a liquid which was purified by column chromatography to afford a colourless liquid (yield 40%).

$^1$H-NMR: δ6.78 (3H, m), 4.38 (1H, m), 3.86 (3H, s), 3.85 (3H, s), 3.06 (1H, m), 2.83 (1H, m), 2.48 (2H, m), 1.58 (2H, m), 1.26 (14H, m), 0.88 (3H, t, b). $^{13}$C-NMR: δ14.15, 22.7, 23.56, 29.27, 29.29, 29.4, 29.43, 31.89, 38.66, 39.8, 55.88, 55.91, 77.3, 111.22, 112.53, 121.26, 129.09, 148.03, 148.92. CI-MS: $\{M+1\}^+$ 337 (20), $\{M+1-H_2O\}^+$ 319 (70), $\{C_9H_{11}O_2\}^+$ 151 (100); EI-MS: {M} 336 (100), $\{C_9H_{11}O_2\}$ 151 (50).

Demethylation of 2-hydroxy-1-(3,4-dimethoxyphenyl) dodecan-3-one can be carried out by using $BBr_3$ as a reagent to produce a final product as shown in reaction scheme below. The synthetic procedure will generally follow a published method by which 1 mole of $BBr_3$ may be used to demethylate approximate 3 moles of 2-hydroxy-1-(3,4-dimethoxyphenyl)dodecan-3-one at room temperature (Bhatt and Kulkarni, 1983). This may result in three products as shown in the reaction scheme below.

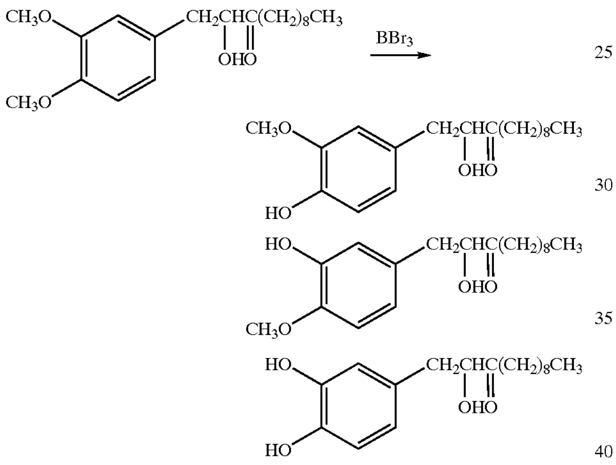

Preparation of 1-(3,4-dimethoxyphenyl)dodecan-2-ol

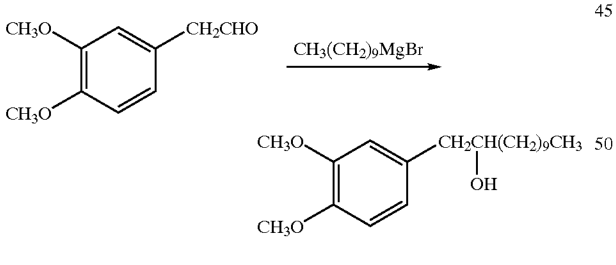

To a Grignard solution of decylmagnesiumbromide, prepared from Mg (0.05 g) and 1-bromodecane (0.36 g), in THF (5 ml) under $N_2$ was added 3,4-dimethoxyphenylacetal (0.5 g) in THF (5 ml). The mixture was stirred at room temperature for 5 hrs. Cold water (10 ml) was added following by the addition of $H_2SO_4$ (1 M, 40 ml). The mixture was extracted twice with diethylether (50 ml), washed with brine solution and the solvent evaporated to give a liquid which was purified by column chromatography to afford a colourless solid (yield 60%).

$^1$H-NMR: δ6.74–6.82 (3H,m), 3.88 (3H, s), 3.86 (3H, s), 3.78 (1H, m), 2.77 (1H, m), 2.57 (1H, m), 1.52 (2H, m), 1.26 (16H, m), 0.88 (3H, t, b). $^{13}$C-NMR: δ14.17, 22.73, 25.84, 29.83, 29.67 (3C), 29.74, 31.96, 36.88, 43.66, 55.88, 55.96, 72.75, 111.37, 112.58, 121.35, 131.15, 147.71, 148.99. CI-MS: $\{M+1\}^+$ 323 (25), $\{M+1-H_2O\}^+$ 305 (100), $\{C_9H_{11}O_2\}^+$ 151 (15); EI-MS: {M} 322 (100), $\{C_9H_{12}O_2\}$ 152 (50).

Demethylation can be carried out as described above for 2-hydroxy-1-(3,4-dimethoxyphenyl)dodecan-3-one. This may also result in three products.

Preparation of 2-hydroxy-1-(3,4-dimethoxyphenyl) undecan-4-one

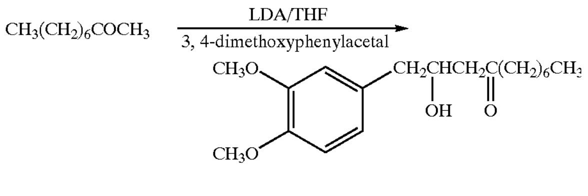

The title compound was prepared as described in the preparation of 3-hydroxy-1-(4-hydroxy-3-methoxyphenyl) dodecan-5-one (page 34).

$^1$H-NMR: δ6.74–6.82 (3H,m), 4.26 (1H, m), 3.87 (3H, s), 3.86 (3H, s), 2.62–2.84 (2H, m), 2.37–2.57 (4H, m), 1.55 (2H, m), 1.25 (8H, m), 0.87 (3H, t, b). $^{13}$C-NMR: δ14.1, 22.63, 23.59, 29.07, 29.14, 31.68, 42.51, 43.75, 48.14, 55.9, 55.94, 68.85, 111.29, 112.55, 121.37, 130.48, 147.78, 148.95. CI-MS: $\{M+1\}^+$ 323 (10), $\{M+1-H_2O\}^+$ 305 (40), $\{C_{10}H_{13}O_3\}^+$ 181 (80), $\{C_9H_{19}O\}^+$ 143 (85); EI-MS: {M} 322 (100), $\{M-H_2O\}$ 304 (90), $\{C_{11}H_{13}O_2\}$ 177 (60), $\{C_9H_{11}O_2\}$ 151 (50).

Demethylation can be carried out as described above for 2-hydroxy-1-(3,4-dimethoxyphenyl)dodecan-3-one. This may also result in three products.

A. Sarcoplasmic Reticulum $Ca^{2+}$-ATPase Assay

SR membrane (75 μg/ml): 24 μl

Test substance: appropriate volumes to give a dose-effect concentration

Incubation buffer: up to 240 μl

A portion at each concentration (54 μl) was aliquoted into 4 designated wells of the microplate (two of four wells were controls). Each well was mixed with ATP solution (20 mM, 6 μl), except the controls, using an 8 channel pipette. The controls were assayed in the absence of ATP or calcium.

The plate was incubated with the lid on, for 30 min at 37° C., colour reagent (160 μl) was then added and mixed with citrate solution (34%, 30 μl). The plate was developed at room temperature for 30 min then absorbance at 655 nm was read from the microplate reader. The $Ca^{2+}$-ATPase activity was quantitated, from a $P_i$ standard curve, as concentration of liberated inorganic phosphate.

Stock solutions (10 mM) of test substance were prepared in DMSO, then series dilutions were made either in DMSO or in 1M HEPES to produce the dose-response concentrations. The maximum concentration of DMSO in the final assay solution was 2.5%.

Each concentration of test substance was assayed in duplicate in the presence and absence of ATP or calcium. Phosphate standards are run on each plate as follows:

| | | | | | | | | |
|---|---|---|---|---|---|---|---|---|
| $P_1$ (nmoles/60 μl) | 0 | 1 | 2 | 3 | 4 | 6 | 8 | 10 |
| $P_1$ stock (μl) | 0 | 6 | 12 | 18 | 24 | 36 | 48 | 60 |
| $H_2O$ (μl) | 60 | 54 | 48 | 42 | 36 | 24 | 12 | 0 |

B. Preparation of SR $Ca^{2+}$-ATPase Incubation Buffer

| Buffer concentration | Stock conc. | Volume taken |
|---|---|---|
| 0.1 mM KCl | 2 M | 5 ml |
| 4 mM MgCl | 1 M | 0.4 ml |
| 0.1 M Sucrose | 2 M | 5 ml |
| 5 mM $NaN_3$ | 1 M | 0.5 ml |
| 20 mM Imidazole | 1 M | 2 ml |
| $H_2O$ to 100 ml | | |

pH was adjusted to ~7.4

C. Preparation of SR ATP Solution (10×)

| Final conc. | 10× conc. | Stock conc. | Amount taken |
|---|---|---|---|
| 2 mM ATP | 20 mM | | 0.126 g/10 ml |
| 66 μM $CaCl_2$ | 0.66 mM | 0.1 M | 66 μl |
| 30 μM EGTA | 0.3 mM | 0.1 M | 30 μl |
| SR buffer to 10 ml | | | |

pH was adjusted to ~7.4

D. Preparation of AMT Solution 3 parts of malachite green (0.05%)

1 part ammonium molybdate solution

The mixture was stirred at room temperature for 1 hour then Tween 20 (60 μl per 100 ml) was added and stirred for ½ hour at room temperature.

3.2.5 Organ Bath Assay

Male guinea pigs, 3–4 weeks old, were killed by rapid cervical dislocation without induced anaesthesia. Then, the guinea pigs were dissected to isolate the atria which were immediately mounted vertically in an organ bath containing Krebs-Henseleit solution oxygenated with carbogen.

One gram tension was applied to the atria and the base line continuously adjusted until it was stable for 20 mins. The rate and force of contraction were recorded using Mac Lab equipment.

Test substances in DMSO were assayed to a maximum concentration of 50 μM at a final concentration of 2.5% of DMSO.

Krebs-Henseleit Solution

| | | 1 liter |
|---|---|---|
| I. | $MgSO_4.7H_2O$ | 0.29 g |
| | NaCl | 6.92 g |
| | KCl | 0.35 g |
| | $KH_2PO_4$ | 0.165 g |
| | D-glucose | 2.10 g |
| II. | $NaHCO_3$ | 2.10 g |
| III. | $CaCl_2.2H_2O$ (0.373 g/ml) | 1 ml |

(I) was dissolved in an appropriate volume of phosphate free water, followed by the addition of (II) until all dissolved, then (III).

Results—SR $Ca^{2+}$-ATPase Activity

| Concentration (μM) | [6]-gingerol | [8]-gingerol | [8]-dehydro | 1-(hydroxy-3-methoxy-phenyl) dodecan-3-ol |
|---|---|---|---|---|
| 0 | 100 | 100 | 100 | 100 |
| 1 | 121 | 139 | 93 | — |
| 5 | 120 | 158 | 88 | 102 |
| 10 | 117 | 165 | 92 | 108 |
| 25 | 137 | 200 | 95 | 140 |
| 50 | 160 | 139 | 65 | 101 |
| 100 | — | — | — | 98 |
| 200 | — | — | — | 16 |

| Concentration (μM) | 1-(4-hydroxy-3-methoxyphenyl) dodecan-5-one; | 3-hydroxy-1-(4-hydroxy-3-methoxyphenyl) decan-1-one | 3-hydroxy-1-(4-hydroxy-3-methoxyphenyl) dodecan-1-one |
|---|---|---|---|
| 0 | 100 | 100 | 100 |
| 1 | — | 104 | 122 |
| 5 | 113 | 152 | 111 |
| 10 | 136 | 174 | 133 |
| 25 | 158 | 195 | 147 |
| 50 | 126 | 180 | 158 |
| 100 | 87 | 222 | 149 |
| 200 | 18 | — | — |

Effect of gingerols and their derivatives on the $Ca^{2+}$-ATPase of dog cardiac SR.

Results

Table 1: SR $Ca^{2+}$-ATPase Activity and Inotropic Activity of Gingerols and Gingerol Analogues. $IC_{50}$=conc. for 50% Inhibition.

| COMPOUNDS | SR $Ca^{2+}$-ATPase (μM) | FORCE OF CONTRACT[n] | HEART RATE |
|---|---|---|---|
| [6]-gingerol | ↑60% @ 50<br>$IC_{50}$ > 100 | ↑86% @ 50 | ↑10% @ 50 |
| [8]-gingerol | ↑100% @ 25<br>$IC_{50}$~100 | ↑160% @ 3 | ↑31% @ 3 |
| [8]-dehydrogingerol | ↓35% @ 50<br>$IC_{50}$~50 | ↑80% @ 25 | ↑17% @ 25 |
| [8]-isogingerol | ↑64% @ 50<br>$IC_{50}$ > 100 | inactive | inactive |

-continued

| COMPOUNDS | SR $Ca^{2+}$-ATPase ($\mu$M) | FORCE OF CONTRACT[n] | HEART RATE |
|---|---|---|---|
| [8]-orthogingerol | ↑40% @ 100<br>$IC_{50}$ > 100 | inactive | inactive |
| [6]-demethoxygingerol | $IC_{50}$ > 100 | inactive | inactive |
| [8]-demethoxygingerol | ↑60% @ 50<br>$IC_{50}$ > 100 | inactive | inactive |
| 3-hydroxy-1-(4-hydroxy-3-methoxyphenyl) dodecan-5-one (3.90) | $IC_{50}$ > 100 | ↑130% @ 10<br>↑270% @ 5 | ↑30% @ 10 |
| 3-hydroxy-1-(4-hydroxy-3-methoxyphenyl) decan-1-one (3.92) | ↑95% @ 25<br>$IC_{50}$~50 | ↓11% @ 10<br>↓13% @ 30 | ↓5% @ 10 |
| 3-hydroxy-1-(4-hydroxy-3-methoxyphenyl) dodecan-1-one (3.91) | ↑60% @ 10<br>$IC_{50}$~50 | ↑11% @ 30 | |
| 3-hydroxy-1-(4-hydroxy-3-methoxyphenyl) dodecane | ↑40% @ 25<br>$IC_{50}$ 50–100 | ↑108% @ 10 | ↑50% @ 10 |
| 5-hydroxy-1-(4-hydroxy-3-methoxyphenyl) dodecane (3.94) | ↑57% @ 25<br>$IC_{50}$~25 | ↑79% @ 30 | ↑weakly |
| 1-(4-hydroxy-3-methoxyphenyl)dodecan-3-one | | inactive | inactive |
| [8]-gingerdiol | ↑54% @ 50<br>$IC_{50}$ > 100 | inactive | inactive |
| 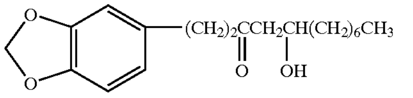 | inactive | | |
| bisgingerol<br>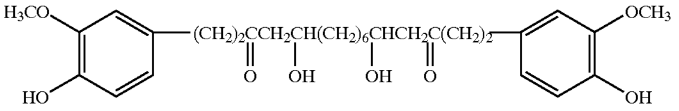 | | inactive | inactive |

↑increase or stimulation
↓decrease or inhibition

Guinea pig atria testing on a range of phenolic substances revealed a number of interesting substances, including gingerols shown in table 1, that give rise to increased contractility of the atria. [8]-Gingerol appeared to be one of the most potent cardiotonic substances in the series. All the test substances increased the heart rate significantly. It was observed that all gingerol derivatives except [8]-dehydrogingerol developed maximum tension rapidly in a min or so after addition of a dose. In contrast, [8]-dehydrogingerol and digoxin took a few mins for tension to reach maximum. Digoxin was observed to cause arrhythmia a few mins after addition of a dose.

Discussion

Substances of the gingerol series may exhibit similar mechanisms of action to those described for fatty acids but with selectivity towards SR $Ca^{2+}$-ATPase only. They produced in general a biphasic activity profile. They stimulate the ATPase at low concentration but weakly inhibit the enzyme at high concentration. SAR of gingerol revealed a unique aromatic feature which is essential for cardiotonic activity. [8]-Gingerol appeared the most potent cardiotonic substance in the series, however, it is readily chemically (Mustafa et al., 1993) and biochemically (Young-Joon, 1994) degraded even in its pure state. Upon storage for a long time or exposure to an acidic environment, dehydration occurs rapidly particular at low pH to produce a shogaol which is devoid of cardiotonic activity. This could be a reason for the apparent short half life of [8]-gingerol when it was given to dogs (0.3 mg/kg, i.v.) resulting in increased cardiac contractility of about 30% for 10 min (Mitsubishi Co, 1982).

Some analogues such as 1-(4-hydroxy-3-methoxyphenyl) dodecan-3-ol, 3-hydroxy-1-(4-hydroxy-3-methoxyphenyl) decan-1-one and 3-hydroxy-1-(4-hydroxy-3-methoxyphenyl)dodecan-1-one are probably chemically and biochemically much more stable than gingerols. Therefore, further investigation of the physicochemical properties as well as mechanism(s) of action of these substances, including gingerols, is required in relation to cardiotonicity. The mode of action of gingerols as cardiotonic agents has been thoroughly investigated and it was proposed that they act by direct stimulation of the cardiac SR $Ca^{2+}$-ATPase. This may load extra calcium into the intracellular stores in the sarcoplasmic reticulum allowing more calcium to be released on stimulation of the heart resulting in increased cardiac contractility. However, this study has indicated that the positive cardiotonicity of gingerols may not be simply related directly to its activation of SR $Ca^{2+}$-ATPase. It was found that [8]-dehydrogingerol, a SR $Ca^{2+}$-ATPase inhibitor, also produced a cardiotonic effect on guinea pig atria, however, the maximum effect was much delayed compared to [8]-gingerol which rapidly produced increased cardiac contractility 15 sec after addition of the drug. This indicated that [8]-gingerol may exert actions outside of the cell in addition to activation of SR $Ca^{2+}$-ATPase. The cardiotonic action of 1-(4-hydroxy-3-methoxyphenyl)dodecan-3-ol [3.93] was confirmed from independent studies, carried out at our request as part of our agreement with Johnson & Johnson Research Ltd (J&J), by Prof. James Angus from the University of Melbourne. Preliminary mechanistic studies, shown in the table below, of the substance revealed that the positive inotropic activity ($1\times10^{-6}$ to $3\times10^{-5}$ in concentrations) of the substance was not due to sympathetic nerve stimulation nor mediated by $\alpha$- or $\beta$-adrenoceptors. It had neither an effect on the neuromuscular junction from phrenic nerve stimulation of rat diaphragm, nor an effect on sympathetic neuro-effector function in the rat vas deferens. A tachycardial effect of the substance on guinea pig atria was, however, observed at significant rate, 50–60% of isoprenaline $E_{max}$ and the response was not α- or β-adrenoceptor mediated. The mechanism of tachycardia and positive inotropic response of the substance was shown to be due to the release of neuropeptides and probably cGRP and indirectly a release of histamine since pretreatment of the guinea pig atria with capsaicin or capsazepine, a capsaicin antagonist, abolished inotropic effect of the test substance. Similarly capsaicin was observed to have tachycardial and inotropic effects on guinea pig atria and these effects were blocked in the presence of either 1-(4-hydroxy-3-methoxyphenyl)dodecan-3-ol or capsazepine.

Cardiovascular and Neuro-effector Junction Activities of Gingerol Analogues

| | right atrium-vagus rat | right atrium rat | left atrium rat | vas deferens rat |
|---|---|---|---|---|
| 3-hydroxy-1-(4-hydroxy-3-methoxy-phenyl) decan-1-one | some enhanced slowing $10^{-6}$–$10^{-5}$ M | no change basal rate $10^{-7}$–$10^{-5}$ M | no change $10^{-7}$–$3 \times 10^{-5}$ M (sharp fall $10^{-4}$ M) | no effect $10^{-4}$ M |
| 1-(4-hydroxy-3-methoxy-phenyl) dodecan-3-ol | dramatic enhancement n = 1 $10^{-6}$–$10^{-5}$ M | tachycardia $3 \times 10^{-7}$–$3 \times 10^{-6}$ M (with propranolol present) | no change in force $10^{-7}$–$10^{-5}$ M (n = 2) | ↓30% $10^{-5}$ M (vehicie?) |

| | diaphragm rat | right atrium-vagus guinea pig | right atrium guinea pig | left atrium guinea pig |
|---|---|---|---|---|
| 3-hydroxy-1-(4-hydroxy-3-methoxy-phenyl) decan-1-one | no effect $10^{-5}$ M ↓10% $3 \times 10^{-5}$ M | weak? enhanced slowing | no change basal rate $10^{-7}$–$10^{-5}$ M | no inotropism no effect on isoprenaline response (up to 30 μM) |
| 1-(4-hydroxy-3-methoxy-phenyl) dodecan-3-ol | ↓10% $10^{-5}$ M (vehicle?) | no enhancement of vagal slowing $10^{-7}$–$10^{-5}$ M | tachycardia $10^{-7}$–$3 \times 10^{-5}$ M to 60% of isopren. Emax (not blocked by praz., prop.) | inotropic $10^{-6}$–$3 \times 10^{-5}$ M ~20% isopren. max. (not in rat) |

Cardiac Electrophysiological Activities of Gingerol and its Analogue

The basic cardiac electrophysiological properties were assessed using cardiac Purkinje fibres obtained from adult mongrel dogs.

3-hydroxy-1-(4-hydroxy-3-methoxyphenyl)decanone (n=3)

| Concentration (μM) | Action Potential Amplitude (mV) | Maximum rate of depolarisation (V/s) | Action Potential Duration 50% repolarisation (ms) | Action Potential Duration 90% repolarisation (ms) |
|---|---|---|---|---|
| 0 | 126 ± 4 | 605 ± 70 | 200 ± 20 | 283 ± 22 |
| 5 | 125 ± 3 | 524 ± 66 | 176 ± 17 | 270 ± 26 |
| 10 | 127 ± 4 | 527 ± 78 | 157 ± 23 | 257 ± 25 |
| 20 | 123 ± 6 | 521 ± 87 | 124 ± 16 | 245 ± 17 |
| 30 | 115 ± 7 | 423 ± 45 | 94 ± 10 | 212 ± 21 |
| 40 | 117 ± 7 | 442 ± 61 | 81 ± 10 | 201 ± 13 |
| 50 | 110 ± 9 | 363 ± 74 | 55 ± 4 | 188 ± 19 |

[8]-gingerol (n=9)

| Concentration (μM) | Action Potential Amplitude (mV) | Maximum rate of depolarisation (V/s) | Action Potential Duration 50% repolarisation (ms) | Action Potential Duration 90% repolarisation (ms) |
|---|---|---|---|---|
| 0 | 123 ± 2 | 576 ± 71 | 278 ± 18 | 385 ± 24 |
| 5 | 124 ± 2 | 532 ± 42 | 242 ± 20 | 363 ± 27 |
| 10 | 120 ± 4 | 483 ± 41 | 207 ± 20 | 339 ± 26 |
| 20 | 119 ± 2 | 499 ± 41 | 142 ± 20 | 285 ± 26 |
| 30 | 114 ± 3 | 443 ± 45 | 107 ± 17 | 248 ± 25 |
| 40 | 116 ± 4 | 516 ± 67 | 88 ± 15 | 229 ± 22 |
| 50 | 109 ± 8 | 471 ± 73 | 76 ± 12 | 221 ± 19 |

Electrophysiology Results

Electrophysiology was carried out on dog heart purkinje fibre to test for potential arrhythmia. [8]-Gingerol and an analogue 3.92, up to 10 μM, caused insignificant effect on the rate of depolarization, amplitude of action potential and duration of action potential at 50% and 90% repolarization. At high concentration (50 μM), however, [8]-gingerol reduced approximate 80% and 50% of action potential duration at 50% and 90% repolarisations respectively. Whereas the analogue reduced 75% and 30% respectively.

Vasodilation of Gingerol Analogues on Rat Mesenteric Artery

Small arteries (200–300 μm in diameter) isolated from rat mesentery were precontracted with endothelin prior to addition of the test substances and tested for relaxation.

Results

| Compounds | $EC_{50}$ (μM) |
|---|---|
| 1-(4-hydroxy-3-methoxyphenyl) dodecan-3-ol | 0.1 |
| enantiomer-1 | 0.5 |
| enantiomer-2 | 0.32 |
| 5-hydroxy-1-(3,4-methylene-dioxyphenyl) dodecan-3-one | 0.69 |
| [8]-paradol | 0.05 |
| 3-hydroxy-1-(4-hydroxy-3-methoxyphenyl) dodecan-5-one | 0.04 |

At $10^{-7}$–$10^{-6}$ M, these substances gave complete relaxation of precontracted blood vessels and the relaxation was probably due to the release of neuropeptide from sensory nerves, however the identity of the peptides responsible for the relaxation is not certain, as yet. The relaxation was abolished by pretreatment with capsaicin and alternatively, pretreament of the gingerol analogues also abolished the vasodilation by capsaicin. Preliminary studies on cultured cells from rat dorsal root ganglion have shown that 1-(4-hydroxy-3-methoxyphenyl)dodecan-3-ol increased intracellular calcium, which is probably a mechanism of action of the gingerol analogues. The rise in intracellular calcium may result in release of neuropeptide(s) from sensory nerves that cause vasodilation of rat mesenteric artery. The exact receptor(s) where gingerol analogues exert their actions remains to be defined. Further investigation is in progress.

Platelet Aggregation Activity of Gingerol Analogues

Blood was collected from healthy volunteers who had taken no medication in the previous two weeks. The anticoagulant used was 3.8% trisodium citrate. Platelet rich plasma was prepared and incubated with [$^3$H]-serotonin. This was followed by addition of gingerol analogues. Platelet activation was initiated using the $EC_{50}$ concentration for arachidonic acid. The percentage of [$^3$H]-serotonin release was measured using a liquid scintillation counter. Then, dose-response curves were established and $IC_{50}$ values were obtained.

Results

| Compounds | $IC_{50}$ ($\mu$M) |
|---|---|
| Aspirin | 23.4 ± 1.7 |
| [6]-gingerol | 73.8 ± 6.6 |
| [8]-gingerol | 70.4 ± 3.8 |
| 1-(4-hydroxy-3-methoxyphenyl) dodecan-3-ol | 58.0 ± 1.9 |
| [8]-gingerdiol | 82.6 ± 9.0 |
| 3-methyl-1-(4-hydroxy-3-methoxyphenyl)undecan-3-ol | 45.3 ± 1.6 |
| 3-methyl-1-(4-hydroxy-3-methoxyphenyl)tridecan-3-ol | 75.3 ± 3.1 |
| 1-hydroxy-1-(4-hydroxy-3-methoxyphenyl)undecan-2-one | 69.4 ± 2.6 |

Neurokinin Activity of Gingerol Analogues 3-hydroxy-1-(4-hydroxy-3-methoxyphenyl)dodecane [3.93], was tested on guinea pig submaxillary membrane for neurokinin-1 (NK-1) antagonist activity with tritium labelled [$^3$H] Substance P and found to have relatively potent inhibition of the binding of Substance P to NK-1 receptor. The substance exhibited a dose-dependent inhibition of Substance P on NK-1 receptor. It gave approximately 80% inhibition at 30 $\mu$M.

Lipoxygenase Activity of Gingerol Analogues 3-hydroxy-1-(4-hydroxy-3-methoxyphenyl)dodecane [3.93] was tested at MDS PANLABS: Pharmacology Services (Taiwan) for 5-lipoxygenase activity from rat basophilic leukemia cells (RBL-1) with arachidonic acid as substrate. The inhibitory activity of the substance was quantitated, using radioimmunoassay, from the formation of 5-HETE. At 10 $\mu$M, the substance gave approximate 90% inhibition of 5-lipoxygenase activity.

Toxicity—Brine Shrimp Assay

The brine shrimp assay procedure determines $LC_{50}$ values of active compounds. Activities of a broad range of known active compounds are manifested as toxicity to brine shrimp (Artemia salina Leach). There are many applications of the assay including analysis of toxic substances, anaesthetics, morphine-like substances and cocarcinogenicity of phorbol esters. The assay shows good correlation with some cytotoxicities and its utility as a prescreen for some antitumour activities has been recently confirmed.

DMSO (dimethyl sulfoxide) was the solvent of choice because of its good solubilising properties and also because the substances used in the ATPase inhibition assays were already prepared with DMSO.

The method for testing solvent toxicity used was basically that reported by J L McLaughlin in *Methods of Plant Biochemistry* (1991), vol. 6 (K Hostettman, ed.), Academic Press, London, 1–32. DMSO solutions of the substances to be tested were added directly to the vials containing the brine shrimp. As the concentration of DMSO is that we wished to use was higher than the recommended 1% v/v testing of the toxicity of the DMSO was therefore necessary. The concentrations of DMSO tested on the shrimp, along with the results from the assay which was done in duplicate are listed below.

Concentrations of DMSO Tested

| Conc (% v/v) | % Deaths |
|---|---|
| 0 | 0 |
| 1 | 0 |
| 2 | 0 |
| 3 | 0 |
| 4 | 0 |
| 5 | 9 |
| 7 | 12 |
| 9 | 18 |
| 11 | 57 |
| 13 | 96 |
| 15 | 100 |
| 20 | 100 |
| 25 | 100 |

Bioassay

Brine shrimp toxicity was assayed, except for some minor modifications, according to the method of McLaughlin et al as reported in Brine Shrimp: A convenient bioassay for active plant constituents, B N Meyer, N R Ferrigni, J E Putnam, L B Jacobsen, D E Nichols and J L McLaughlin in *Planta Medica* (1982), 45, 31–34 and Crown gall tumours on potato discs and brine shrimp lethality: Two simple bioassays for higher plant screening and fractionation. J L McLaughlin. *Methods of Plant Biochemistry* (1991), vol. 6 (K Hostettman, ed.), Academic Press, London, 1–32. Ten shrimp were transferred to each of the vials and the volume adjusted to 4.9 mL. Each dose was performed in triplicate, including the control. In quick succession, the appropriate volume of additional DMSO for each dose, required to achieve a final concentration of 2%, was added before the appropriate volume of test solution. The vials were gently mixed and the time noted. After 24 hours, the number of survivors were counted and % mortality was determined. The test compounds were assayed at concentrations of 100 $\mu$M, 25 $\mu$M, 5 $\mu$M, 1 $\mu$M and 0.2 $\mu$M (and where appropriate concentrations of 0.04 $\mu$M and 0.008 $\mu$M).

The brine shrimp were able to survive without food in the vials over the 24 hour period and were therefore not fed.

The dose-response curves were constructed using the Sigmaplot computer program and the $LC_{50}$ value was calculated from the intersection point of the curve and the 50% mortality line. The $LC_{50}$ values were expressed in both $\mu$M and $\mu$g/mL.

Table 2: $LC_{50}$ Values of Phenolic Substances from Brine Shrimp Bioassay

For substances with low toxicity, the greater sign ">" indicated the highest concentration at which the assay was carried out as precipitation of the substances occurred above that concentration.

| MWt | Compound | $LC_{50}$ μM | $LC_{50}$ μg/ml |
|---|---|---|---|
| 294 | [6]-gingerol | >100 | >29 |
| 322 | [8]-gingerol | 64 | 21 |
| 322 | [8]-orthogingerol | 9.6 | 3.1 |
| 322 | [8]-isogingerol | 11 | 3.5 |
| 322 | 3-hydroxy-1-(4-hydroxy-3-methoxyphenyl)dodecan-5-one | 67 | 22 |
| 294 | 3-hydroxy-1-(4-hydroxy-3-methoxyphenyl)decan-1-one | 66 | 19 |
| 322 | 3-hydroxy-1-(4-hydroxy-3-methoxyphenyl)dodecan-1-one | 10 | 3.2 |
| 320 | [8]-dehydrogingerol | 41 | 13 |
| 264 | 5-hydroxy-1-(4-hydroxyphenyl)decan-3-one | >100 | >26 |
| 292 | 5-hydroxy-1-(4-hydroxyphenyl)dodecan-3-one | 25 | 7.3 |
| 290 | 5-hydroxy-1-(4-hydroxyphenyl)dodecan-1-ene-3-one | 2.6 | 0.75 |
| 308 | 1-(4-hydroxy-3-methoxyphenyl)dodecan-3-ol | >100 | >31 |
| 308 | 1-(4-hydroxy-3-methoxyphenyl)dodecan-5-ol | 6.6 | 2.0 |
| 302 | 1-(4-hydroxy-3-methoxyphenyl)dodecane-1,4-diene-3-one | 5.4 | 1.6 |
| 320 | 5-hydroxy-1-(3,4-methylenedioxyphenyl)dodecan-3-one | 3.0 | 0.96 |
| 414 | podophyllotoxin | 3.8 (5.8)* | 1.6 (2.4) |

*$LC_{50}$ values determined by Meyer et al. (1982)

Discussion

In this bioassay, the estimated $LC_{50}$ value of the test compound indicates its toxicity to brine shrimp. A more useful comparison of potencies can be obtained by looking at the μM instead of μg/mL concentrations in Table 2. Podophyllotoxin was tested in order to check whether the bioassay's results were comparable with those of Meyer et al. The $LC_{50}$ from this study was 3.8 μM and is reasonably close to the $LC_{50}$ value of 5.8 μM determined by Meyer et al.

Effect of Gingerol Analogues Towards Rat Dorsal Root Ganglia

Capsaicin, the pungent component in peppers of the Capsicum genus, family Solanaceae, has the ability to excite a subset of sensory neurons, which include polymodal nociceptors and warm thermoceptors (Fitzgerald, 1983) by opening non-selective cation channels that are permeable to $Na^+$, $K^+$, and $Ca^{2+}$ (Bevan and Szolcsanyi, 1990). It has been shown that capsaicin evoked a concentration-dependent rise in $[Ca^{2+}]_i$ in cultured dorsal root ganglion neurons. The duration of the elevation of $[Ca^{2+}]_i$ depended on the concentration of capsaicin (Choleswinski, et al., 1993). In this investigation peak $[Ca^{2+}]_i$ transient measurements are used as a model for testing gingerol analogues.

EXPERIMENTAL

DRG from neonatal (3–5 days old) rat or adult Sprague-Dawley rats were incubated in Hanks CMF saline with 0.05% collagenase and 0.25% trypsin for 25 min at 37° C. Individual cells were obtained by trituration with fire polished Pasteur pipettes of diminishing diameters. Neurones were isolated from the cell suspension in 30% Percoll and then plated on collagen coated coverslips or in 24-well plates, then cultured in neurobasal medium with B27 supplement, 50 ng/ml 2.5 S nerve growth factor, 2 mM 1-glutamine and 100 U/ml penicillin/streptomycin. Cultures were maintained at 37° C. with 5% $CO_2$. 30% Percoll increases the percentage of capsaicin-sensitive DRG neurones up to 70%. For peak $[Ca^{2+}]_i$ transients measurements, cells on coverslips were incubated with 5 μM Fura-2 AM for 30 min at 37° C. The coverslips were then mounted on a chamber attached to a fast sample application perfusion system which allows changing solutions in the second range. Recordings were made on the stage of a Nikon Diaphot inverted microscope fitted with a Nikon 40×Fluo (NA 0.85) DL Ph3 or 40×Fluo (NA 1.3) oil objective. $[Ca^{2+}]_i$ was calculated from dual excitation wavelength (340/380 nm) fluorescence measurements following an intracellular calibration procedure by the Grynkiewicz equation, using MCID M2/M4 v.3.0 (Imaging Res. Inc.) software. Cells were continuously perfused with a solution consisting of 140 mM NaCl, 2 mM $CaCl_2$, 5 mM KCl, 20 mM HEPES, 10 mM glucose, pH 7.4. To study KCl evoked depolarisation, 50 mM NaCl was replaced by equimolar KCl. Cytoplasmic localisation of Fura-2 was tested with the $Mn^{2+}$ quenching technique (Dedov and Roufogalis, 1998). All experiments were performed at room temperature (20–23° C.).

Results

Typical changes in $[Ca^{2+}]_i$ upon depolarisation were evoked by 50 mM KCl and by application of 1 μM capsaicin; both were applied for 30 sec. Capsaicin-evoked peak $[Ca^{2+}]_i$ transients are characterised by a fast rise and long-steady state $[Ca^{2+}]_i$ clearance from the cytoplasm. In capsaicin-sensitive cells the half-time of cytoplasmic $Ca^{2+}$ clearance was proportional to the amplitudes of peak $[Ca^{2+}]_i$ transients.

To examine the effect of gingerol derivatives, one or several compounds in succession at a concentration of 10 μM were applied for 1 min to the DRG neuronal cells followed by washing out for 4 min with physiological solution. To the capsaicin-sensitive cells, 10 μM capsaicin and 50 mM KCl were applied, respectively, to confirm the viability of the cells. In addition, morphological appearances of the cells were also examined at the end of experiment. All experiments were carried out in the presence of 2 mM $Ca^{2+}$.

Effect of the Gingerol Analogues and Capsaicin in Evoking $[Ca^{2+}]_i$ Transients in DRG Neuronal Cells in Culture

| Name of compounds | Number of capsaicin-sensitive cells responding | Peak $[Ca^{2+}]_i$ (nM) (Average ± SD) |
|---|---|---|
| Capsaicin | 5 | 824 ± 122 (high responses) |
| | 10 | 134 ± 78 (low responses) |
| 1-(4-hydroxy-3-methoxyphenyl) dodecan-3-ol | 5 | 661 ± 376 (high responses) |
| | 10 | 187 ± 66 (low responses) |
| 3-hydroxy-1-(4-hydroxy-3-methoxyphenyl) dodecan-5-one | 5 | 167 ± 105 |
| 5-hydroxy-1-(4-hydroxy-3-methoxyphenyl) dodecan-3-one | 7 | 279 ± 111 |
| 5-hydroxy-1-(3-hydroxy-4-methoxyphenyl) dodecan-3-one | 2 | 281 ± 42 |

-continued

| Name of compounds | Number of capsaicin-sensitive cells responding | Peak $[Ca^{2+}]_i$ (nM) (Average ± SD) |
|---|---|---|
| 5-hydroxy-1-(2-hydroxy-3-methoxyphenyl) dodecan-3-one | 2 | 245 ± 64 |
| 5-hydroxy-1-(4-hydroxyphenyl) dodecan-3-one | 2 | 243 ± 71 |
| 5-hydroxy-1-3,4-methylenedioxyphenyl) dodecan-3-one | 2 | 225 ± 78 |
| 1-(4-hydroxy-3-methoxyphenyl) dodecane-3,5-diol | 2 | 246 ± 35 |
| 2-hydroxy-1-(4-hydroxy-3-methoxyphenyl) undecan-1-one | 2 | 215 ± 7 |
| [8]-shogaol | 2 | 110 ± 56 |
| [8]-paradol | 1 | 200 |
| 3-hydroxy-1-(4-hydroxy-3-methoxyphenyl) decan-1-one | 0 out of 5 | 0 |
| 3-methyl-1-(4-hydroxy-3-methoxyphenyl) undecan-3-ol | 0 out of 4 | 0 |
| 1-(4-hydroxy-3-methoxyphenyl) dodecan-5-ol | 0 out of 5 | 0 |

All gingerol derivatives at 10 μM, except the last three compounds, evoked $[Ca^{2+}]_i$ transients in capsaicin-sensitive cells.

No capsaicin-insensitive DRG neuronal cells responded to the gingerol derivatives. There are some preliminary indications that gingerol derivative evoked $[Ca^{2+}]_i$ transients have a faster $[Ca^{2+}]_i$ clearance from the cytoplasm, compared to the slow decay of $[Ca^{2+}]_i$ from capsaicin evoked $[Ca^{2+}]_i$ transients. Either different affinities of these compounds for the receptor in comparison to capsaicin, or interaction with sub-populations/classes of receptors or additional stimulation of $[Ca^{2+}]_i$ efflux from the cells were proposed to account for these differences. Both capsaicin and 1-(4-hydroxy-3-methoxyphenyl)dodecan-3-ol evoked $[Ca^{2+}]_i$ transients were abolished or greatly diminished in $Ca^{2+}$-free medium or on the application of ruthenium red (1 μM), a non-specific capsaicin antagonist.

Conclusion

1. The data obtained suggest that 11 (out of the 14 gingerol derivatives tested) may bind to capsaicin-receptor in DRG neuronal cells in culture, subsequently opening ion channel(s) which are permeable to extracellular $Ca^{2+}$. The rise in intracellular $Ca^{2+}$ in cells is known to mediate many biological events, particularly the signal transduction pathway which may lead to release of neuropeptides or factors that subsequently modulate pain transmission mechanisms. A rise in intracellular $Ca^{2+}$ is also known for capsaicin to result in desensitisation of nerve fibres toward further firing from pain stimuli.
2. There is structural specificity, particularly at the hydroxy moiety on the side chain, to evoke $[Ca^{2+}]_i$ transients in DRG neuronal cells from the gingerol derivatives. Despite the very close structural resemblance between 1-(4-hydroxy-3-methoxyphenyl)dodecan-3-ol and 3-methyl-1-(4-hydroxy-3-methoxyphenyl)undecan-3-ol, the former showed a significant rise in $[Ca^{2+}]_i$, whereas the latter was ineffective. These data will direct future synthesis of more effective gingerol derivatives.
3. The difference in $[Ca^{2+}]_i$ clearance from cytoplasm between capsaicin and gingerol derivatives may make the latter less neurotoxic than capsaicin because neurotoxicity is $Ca^{2+}$ dependent (Caterina et: al, 1997)

Cyclo-oxygenase Assay

Cyclooxygenase (COX) is a haemprotein which catalyses the formation of $PGH_2$ from arachidonic acid. Two isoforms of COX have been-identified and designated as COX-1 and COX-2. COX-1 is constitutively expressed in most tissue and performs a "housekeeping" function to synthesise prostaglandins which regulate normal cell activities including antithrombogenic activity and cytoprotection of gastric mucosa and kidney. COX-2 is an inducible enzyme which responds more rapidly and transiently to mediators of immunity, inflammation and tissue repair. Recently attention has been paid to the activity of COX-2 with increased evidence that downregulation of this enzyme activity will be important in control of inflammation and pain and an important strategy for preventing cancer since the enzyme catalyses the formation of prostaglandins which respectively mediate inflammation, pain, and have multiple effects that favour tumorigenesis. Selective inhibition of COX-2 will have many therapeutic applications without causing many undesirable effects to normal cell function.

Cyclo-oxygenase (COX) assay was performed with cells in culture prepared from rat basophilic leukemia (RBL) 2H3 cell lines. Cells were cultured in EMEM containing 10% fetal calf serum and antibiotic until cells reached confluence. Harvested cells were subsequently seeded on 24-well plates at $1\times10^6$ cells/ml then incubated at 37° C. for 3 hours. Cells were washed twice with incubation buffer (1.5 ml) containing 5 mM Hepes, 140 mM NaCl, 5 mM KCl, 0.6 mM $MgCl_2$, 1 mM $CaCl_2$ and 55 mM glucose. Cells were then covered with 0.49 ml of buffer, followed by addition of samples/solvents (0.005 ml) and incubated at 37° C. for 5 min on an orbital shaker. Arachidonic acid (0.005 ml, containing 50% EtOH) was subsequently added, and the plate was incubated at similar conditions for a further 10 min. The supernatant (0.1 ml) was aliquoted for methoxime derivatisation of $PGD_2$, which was carried out by heating the supernatant with methoxime solution (1:1) at 60° C. for 30 min according to the instructions provided with the kit. The resultant solution was diluted with EIA buffer and stored on ice for EIA, following the protocol provided with the kit. Validation of COX enzyme activity was carried out using EIA in which the enzyme activity was characterised against various concentrations of AA and a time course of enzyme activity. All compounds were dissolved in DMSO and assayed at a final concentration of 10 μM. Indomethacin was used as reference compound. The concentration of DMSO in the assay was maintained at 1.5%.

Lipoxygenase Assay

Lipoxygenases, including 5-, 12-, and 15-lipoxygenases and their products play enormous roles in maintaining cellular function. However, they are also the key factors that cause many pathophysiological conditions. Inhibition of these enzymes hence has many therapeutic applications in the treatment of inflammatory, allergic, cardiovascular and skin diseases.

Among these enzymes, 5-lipoxygenase and their products, particularly the leukotriene series, are the most important and extensively studied, revealing that the enzyme and its products mediate certain respiratory, cardiovascular, renal, gastrointestinal, and CNS disorders. The principal therapeutic targets for 5-lipoxygenase inhibitors include allergic diseases, in particular, human bronchial asthma; chronic inflammatory diseases; myocardial ischemia; and inflammatory associated pain.

Lipoxygenase (LP) assay was performed with cell-free enzyme (Wong et al, 1991) prepared from rat basophilic leukemia (RBL) 2H3 cell lines. Cells were cultured in EMEM containing 10% fetal calf serum and antibiotic until cells reached confluence. Harvested cells were resuspended in Hepes (10 mM) buffer, pH 7.4, containing 1 mM EDTA at $1\times10^7$ cells/ml, and disrupted by nitrogen cavitation using a Parr bomb at 750 psi for 15 min. The broken cells were centrifuged at 15,000 g for 30 min. Aliquots (0.1 ml) of the supernatant were preincubated with or without drugs in Hepes buffer (10 mM Hepes, pH 7, 1 mM EDTA and 150 mM NaCl) for 5 min, and the reaction was initiated with the addition of 50 $\mu$l of $CaCl_2$ (16 mM), 50 $\mu$l of ATP (2 mM), 5 $\mu$l of PAF (2.5 mg/ml) and 5 $\mu$l of AA (2.5 mM). The reaction mixture (1 ml in total) was incubated at room temperature for a further 8 min, then diluted with EIA buffer at 1/200 and 1/2000 dilutions and stored on ice for EIA following the protocol provided with the kit. Validation of LP enzyme activity was carried out by a UV spectrophotometric method in which the enzyme activity was characterised against various concentrations of $Ca^{2+}$, ATP, PAF and AA with the measurement of the formation of diene conjugated products of LP at 235 nm.

All compounds were dissolved in DMSO and assayed at a final concentration of 10 $\mu$M. NDGA was used as reference compound. The concentration of DMSO in the assay was maintained at 1.5%.

Results

| Name of compounds | Cyclo-oxygenase activity % activity | Lipoxygenase activity % activity |
|---|---|---|
| 1-(4-hydroxy-3-methoxyphenyl)dodecan-3-ol | 9 | 31 |
| 3-hydroxy-1-(4-hydroxy-3-methoxyphenyl)dodecan-5-one | 18 | 193 |
| 5-hydroxy-1-(4-hydroxy-3-methoxyphenyl)dodecan-3-one | 16 | 65.5 |
| 5-hydroxy-1-(4-hydroxy-3-methoxyphenyl)decan-3-one | 55 | 202 |
| 5-hydroxy-1-(4-hydroxy-3-methoxyphenyl)dodecan-1-ene-3-one | 19 | 37 |
| 5-hydroxy-1-(3-hydroxy-4-methoxyphenyl)dodecan-3-one | 23 | 8 |
| 5-hydroxy-1-(2-hydroxy-3-methoxyphenyl)dodecan-3-one | 17 | 118 |
| 5-hydroxy-1-(4-hydroxyphenyl)dodecan-3-one | 63 | 450 |
| 5-hydroxy-1-(3,4-methylenedioxyphenyl)dodecan-3-one | 59 | 107 |
| 1-(4-hydroxy-3-methoxyphenyl)dodecane-3,5-diol | 10 | 26 |
| 1-hydroxy-1-(4-hydroxy-3-methoxyphenyl)undecan-2-one | 16 | 83 |
| 2-hydroxy-1-(4-hydroxy-3-methoxyphenyl)undecan-1-one | 95 | 61 |
| [8]-shogaol | 21 | 0 |
| 1-(4-hydroxy-3-methoxyphenyl)dodecane-1,4-diene-3-one | | 2 |
| [8]-paradol | 11 | 81 |
| 3-hydroxy-1-(4-hydroxy-3-methoxyphenyl)decan-1-one | 123 | 175 |
| 3-methyl-1-(4-hydroxy-3-methoxyphenyl)undecan-3-ol | 15 | 3 |
| 3-methyl-1-(4-hydroxy-3-methoxyphenyl)tridecan-3-ol | | 5 |
| 1-(4-hydroxy-3-methoxyphenyl)dodecan-5-ol | 12 | 35 |
| Indomethacin (1 $\mu$M) | 23 | |
| NDGA (0.5 $\mu$M) | | 20 |

There are structure-specific activities of the gingerol derivatives in inhibition of cyclooxygenase (COX) and lipoxygenase (LP). It was observed that alteration of the aromatic moiety and/or the functional group on the side chain of the gingerol derivatives severely altered the inhibitory activity of the compounds towards LP. This was, however, not the case in the inhibition of COX. Double bonds and methyl branches on the side chain seem to effectively enhance inhibitory potency of the gingerol derivatives towards lipoxygenase. These results in relation to the inhibition of cyclo-oxygenase and lipoxygenase of the gingerol derivatives, particularly gingerols and shogaol, support the traditional use of ginger in the treatment of inflammatory diseases and associated pain.

The effective amount of the active compound required for use in the above conditions will vary both with the route of administration, the condition under treatment and the host undergoing treatment, and is ultimately at the discretion of the physician. In the above mentioned treatments, it is preferable to present the active compound as a pharmaceutical formulation. A pharmaceutical formulation of the present invention comprises the active compound together with one or more pharmaceutically acceptable carriers and optionally any other therapeutic ingredient. The formulation may conveniently be prepared in unit dosage form and may be prepared according to conventional pharmaceutical techniques. Additionally, the formulations may include one or more accessory ingredients, such as diluents, buffers, flavouring agents, binders, disintegrants, surface active agents, thickeners, lubricants, preservatives, enteric coatings and the like.

Pharmaceutical Formulation

A typical tablet formulation comprises 20–50 mg of the active constituent, 50–200 mg of lactose, 5–30 mg of maize starch and 0.2–1 mg of magnesium stearate. Preferably, the tablet formulation comprises 20–50 mg of the active constituent, about 100 mg of lactose, about 15 mg of maize starch and about 0.5 mg of magnesium stearate.

Modified Ginger Extract Formulation

The modified ginger extract can be administered in a liquid formula or syrup formulation. A typical liquid formula comprises 50–500 mg of extract in alcohol (max. 80% v/v) or glycerol, or in a sugar base preparation (1:1 liquid to sugar ratio). Alternatively, modified ginger extract can be administered in a solid dosage form, which can be either as tablet, capsule, or powder. A typical tablet formulation comprises 50–500 mg of the modified ginger extract, 5–30 mg of maize starch or microcrystalline cellulose and 0.2–1 mg of magnesium stearate. Preferably, the tablet formulation comprises 50–500 mg of the extract, about 15 mg of maize starch or cellulose and about 0.5 mg of magnesium stearate. Capsule or powder dosage forms also contains 50–500 mg of the modified ginger extract. Enteric coatings to protect against degradation may be desirable.

REFERENCES

Aeschbach, R; Loliger, J; Scott, B C; Murcia, A; Butler, J; Halliwell, B and Aruoma, O I. Antioxidant actions of thymol, carvacrol, [6]-gingerol, zingerone and hydroxytyrosol. *Food and Chemical Toxicology* (1994), 32, 31–36.

Antiplatelet Trialists' Collaboration. Collaborative overview of randomised trials of antiplatelet therapy. I: Prevention of death, myocardial infarction, and stroke by prolonged antiplatelet therapy in various categories of patients. *BJM* (1994), 308, 81–106.

Belan, A; Bolte, J; Fauve, A; Gourcy, J G; and Veschambre, H. (1987) Use of biological system for the preparation of chiral molecules. 3. An application in pheromone synthesis: preparation of sulcatol enantiomers. *Journal of Organic Chemistry* 52, 256–260.

Bevan, S and Szolcsanyi, J. Sensory neuron-specific actions of capsaicin: mechanisms and applications. *Trends Neurosci.* (1990), 11, 330–333.

Bevan, S., Hothi, S., Hughes, G., James, I. F., Rang, H. P., Shah, K., Walpole, C. S. J. and Yeats, J. C. Capsazepine: a competitive antagonist of the sensory neurone excitant capsaicin. *Br. J. Pharmacol.* (1992), 107, 544–552.

Bhatt, M V and Kulkarni, S U. Cleavage of ethers. Synthesis (1983), 249–282.

Caterina, M J; Schumacher, M A; Tominaga, M; Rosen, T A; Levine, J D and Julius, D. (1997) The capsaicin receptor: a heat-activated ion channel in the pain pathway. *Nature* 389, 816–824.

Cholewinski, A; Burgess, G M and Bevan, S. The role of calcium in capsaicin-induced desensitisation in rat cultured dorsal root ganglion neurons. *Neurosci.* (1993), 55, 1015–1023.

Crout, D H G; Dalton, H; Hutchinson, D W and Miyagoshi, M. (1991) Studies on pyruvate decarboxylase: Acyloin formation from aliphatic, aromatic and heterocyclic aldehydes. *Journal of the Chemical Society. Perkin transactions I* 1329–1334.

Dedov V. N. and Roufogalis B. D. (1998) Rat dorsal root ganglion neurons express different capsaicin-evoked $Ca^{2+}$ transients and permeabilities to $Mn^{2+}$. *Neuroscience Letter* (1998) 248, 151–154.

Deniff, P; Macleod, I; Whiting, D A. Syntheses of the (±)-gingerols (pungent principles of ginger) and related compounds through regioselective aldol condensations: Relative pungency assays. *J. Chem Soc. Perkin I* (1981), 82–87.

Duke, C. C and Wells, R. J. Investigation of readily available chiral compounds for preparative scale resolutions. *Aust. J. Chem.* (1987), 40, 1641–1654.

Faber, K. Biotransformations in organic chemistry. 2nd Ed. (1995), pages 145–180.

Fitzgerald, M. Capsaicin and sensory neurons—a review. Pain (1983), 15, 109–130.

Hauser, C. R.; Taylor, H. M. and Ledford, G. T. Benzylation and related alkylation of α-dimethylaminophenylacetonitrile by mean of alkali: dehydrocyanation of products to form enamines. *J. Am. Chem. Soc.* (1960), 82, 1786–1789.

Hikino, H; Kiso, Y; Kato, N; Hamada, Y; Shioiri, T; Aiyama, R; Itokawa, H; Kiuchi, F and Sankawa, U. Antihepatotoxic actions of gingerols and diarylheptanoids. *J. Ethnopharmacol.* (1985) 14, 31–39.

Imamura, M., Smith, N. C., Garbarg, M. and Levi, R. Histamine H3-receptor-mediated inhibition of calcitonin gene-related peptide release from cardiac C fibers. A regulatory negative-feedback loop. *Circul. Res.* (1996), 78, 863–869.

Kobayashi, M., Ishida, Y., Shoji, N. and Ohizumi, Y. Cardiotonic action of [8]-gingerol, an activator of the $Ca^{2+}$-pumping adenosine triphosphatase of sarcoplasmic reticulum, in guinea pig atrial muscle. *J. Pharmacol. Exper. Ther.* (1988), 246, 667–673.

Kobayashi, M., Shoji, N. and Ohizumi, Y. Gingerol, a novel cardiotonic agent, activates the $Ca^{2+}$-pumping ATPase in skeletal and cardiac sarcoplasmic reticulum in Guinea pig atrial muscle. *Biochim. Biophys. Acta* (1987), 903, 96–102.

Kimura, I; Pancho, L-R; Shioiri, T and Kimura, M. Suppression of spontaneous calcium spikes and contraction in isolated portal veins in mice by gingerols and chemically related compounds. *Japan. J. Pharmacol.* (1988), 48, 257–262.

Masuda, T; Jitoe, A and Mabry, T J. Isolation and structure determination of cassumunarins A, B, and C: new anti-inflammatory antioxidants from a tropical ginger, Zingiber cassumunar. *J. Am. Oil Chem. Soc.* (1995), 72, 1053–1057.

Meiji Seika Kaisha. (1989) New 6-nor-gingerol used as 5-lipoxygenase inhibitor in medicines. (C89-053141). JP 89-119470/16.

Mitsubishi Chemical Industries Co., Ltd. Gingerols as cardiotonic agents. Jpn. Kokai Tokkyo Koho JP 82 59,809, Apr. 10, 1982, 4 pp. (Chemical Abstracts (1982), 97:33378k).

Miyashita, M; Yoshikoshi, A. and Grieco, P A. Pyridinium p-toluenesulfonate. A mild and efficient catalyst for the tetrahydropyranylation of alcohols. *J. Org. Chem.* (1977), 42, 3772–3774.

Munsiff, A V; Chander, P N; Levine, S and Stier C T. The lipoxygenase inhibitor phenidone protects against proteinuria and stroke in stroke-prone spontaneously hypertensive rats. *Am. J. Hypertens.* (1992), 5, 56–63.

Mustafa, T; Srivastava, K C and Jensen, K B. Drug development report (9): Pharmacology of ginger, *Zingiber officinale. J. Drug Dev.* (1993), 6, 25–39.

Normura, H. The pungent principles of ginger. Part I. A new ketone, zingerone (4-hydroxy-3-methoxyphenylethyl methyl ketone) occurring in ginger. *J. Chem. Soc.* (1917), 111, 769–776.

Noyori, R. and Takaya, T. (1990) BINAP: An efficient chiral element for asymmetric catalysis. *Accounts of chemical research* 23, 345–350.

Onogi, T; Minami, M; Kuraishi, Y and Satoh, M. Capsaicin-like effect of [6]-shogaol on substance P-containing afferents of rats: A possible mechanism of analgesic action. *Neuropharmacology* (1992), 31, 1165–1169.

Roderick, P J; Wilkes, H C and Meade, T W. The gastrointestinal toxicity of aspirin: an overview of randomised controlled trials. *British J. Clin. Pharmacol.* (1993), 35, 219–226.

Salmo, R. Treatment guidelines for hypertension criticised. *Pharmacy Times* (1995), January, 28–33.

Sawamura, S; Mizuta, T and Shirakami, Y. Cardiotonics containing gingerol derivatives. (Nippon Kokan Kk) Jpn. Kokai Tokkyo Koho JP 06,40,895 [94,40,895], 5 pp, (Chemical Abstracts (1994) 121:26913s).

Suekawa, M; Ishige, A; Yuasa, K; Sudo, K; Aburada, M and Hosoya, E. Pharmacological studies on ginger. I. Pharmacological actions of pungent constituents, [6]-gingerol and [6]-shogaol. *J. Pharmacobio-Dyn.* (1984), 7, 836–848.

Suekawa, M; Sone, H; Sakakibara, I; Ikeya, Y; Aburada, M and Hosoya, E. Pharmacological studies on ginger. V. Pharmacological comparison between [6]-shogaol and capsaicin. Nippon Yakurigaku Zasshi (1986), 88, 339–347.

Takeda, S; Aburada, M; Asami, A; Ishihara, K; Fujiwara, T and Ichikawa, Y. Preparation of 1-(4-hydroxy-3-methoxyphenyl)-4-decen-3-ol from [6]-shogaol as 5-lipoxygenase inhibitor. (Tsumura and Co., Japan) WO 9215543, 24 pp. (Chemical Abstracts (1993) 118:124194).

Tanaka, M; Urano, F and Tani, T. Phenolic ketone derivatives. (Wako Pure Chemical Industries, Ltd., Japan; Tsumura Juntendo, Inc.). Jpn. Kokai Tokkyo Koho JP 61134338, 10 pp. (Chemical Abstracts (1987), 106:4657).

Terumo Corporation. (1992) Inhibitor of interleukin-1 production containing gingerol derivatives—for treating inflammation and rheumatoid arthritis. (C92-131350). JP 92-295320/36.

Terumo Corporation. (1992) Agent comprising 3-(3,4-dihydroxyphenyl)propan-1-one gingerol derivatives—for treatment of hepatopathy, especially viral hepatitis. (C92-131351). JP 92-295321/36.

Tran, V H. Structure-activity relationship and

Wood, J. N.; Winter, J.; James, I. F.; Rang, H. P.; Yeats, J. and Bevan, S. Capsaicin induced ion fluxes in dorsal root ganglion cells in culture. *Journal of Neuroscience* (1988), 8, 3208–3220.

Wrigglesworth, R.; Walpole, C. S. J.; Bevan, S.; Campbell, E. A.; Dray, A.; Hughes, G. A.; James, I.; Masdin, K. J. and Winter, J. Analogues of Capsaicin with Agonist activity as Novel Analgesic Agents: Structure-Activity Studies. 4. Potent, Orally active analgesics. *J. Med. Chem.* (1996), 39, 4942–4951.

Yamahara, J.; Hatakeyama, S.; Kawamura, M. and Yoshikawa, M. Stomachic principles in ginger. II. Pungent and anti-ulcer effects of low polarity constituents isolated from ginger, the dried rhizoma of *Zingiber officinale* Roscoe, cultivated in Taiwan. The absolute stereochemistry of a new diarylheptanoid. *Yakugaku Zasshi* (1992), 112, 645–655.

Yoshikawa, M.; Hatakeyama, S.; Taniguchi, K.; Matuda, H. and Yamahara, J. [6]-Gingesulfonic acid, a new anti-ulcer principle, and gingerglycolipids A, B and C, three new monoacylgalactosylglycerols from *Zingiberis rhizoma,* originating in Taiwan. *Chem. Pharm. Bull.* (1992), 40, 2239–2241.

Surh, Y.-J. and Lee, S. S. Enzymatic reduction of [6]-gingerol, a major pungent principle of ginger, in the cell-free preparation of rat liver. *Pharmacology Letters, Life Sciences* (1994), 54, PL 321–326.

Surh, Y.-J. and Lee, S. S. Enzymatic reduction of shogaol: A novel biotransformation pathway for the α,β-unsaturated ketone system. *Biochemistry International* (1992), 27, 179–187.

The claims defining the invention are as follows:

1. A compound of formula (I) or a pharmaceutically acceptable derivative thereof:

(I)

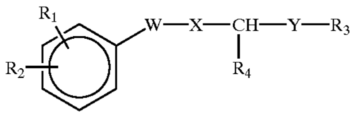

where $R_1$ is H, OH, $OC_{1-4}$alkyl, $NO_2$ $R_2$ is OH, $OC_{1-4}$alkyl, $OC{=}OC_{1-4}$alkyl or OC═OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, ═O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, ═O, nitro, halogen, —NRR', —COOR or —CONRR' where R and R' are H or $C_{1-4}$alkyl;

$R_4$ is H, $CH_3$, OH or ═O; when $R_4$ is ═O, then the carbon to which $R_4$ is attached is not bonded to H;

W is C(═O)—$CH_2$, CH═CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)$ OH, $CH_2$, $CH(CH_3)$ or —C═O;

Y is —CH—OH, $C(CH_3)OH$, $CH_2$, $CH(CH_3)$ or —C═O;

provided that one of W, X or Y has an OH group and provided that when (1) $R_1$ is $OC_{1-4}$alkyl, $R_2$ is OH or OAcyl, W=$CH_2CH_2$ and X=C═O, $R_3$ is $C_{2-12}$ alkyl, $R_4$ is H, then Y is not CHOH (gingerols);

(2) $R_1$ is $OCH_3$, $R_2$ is OH, W is $CH_2CH_2$, $R_3$ is $C_5$ or $C_7$ alkyl, $R_4$ is H and X=CHOH then Y is not CHOH (gingerdiol);

(3) $R_1$ is $OCH_3$, $R_2$ is OH, W is CH═CH, $R_3$ is $C_{2-12}$ alkyl, $R_4$ is H and X is C═O, then Y is not CHOH (dehydrogingerols);

(4) $R_1$ is $OCH_3$, $R_2$ is OH, W=$CH_2CH_2$, X is CHOH, $R_4$ is H and $R_3$ is $C_5$ alkyl then Y is not $CH_2$ (reduced paradol);

(5) $R_1$ is $OCH_3$, $R_2$ is OH, W=$CH_2CH_2$, X is C=O, $R_4$ is H then Y is not $C(OH)CH_3$;

(6) $R_1$ is $OC_{1-4}$ alkyl, $R_2$ is OH or OAcyl, W=CH═CH and X=C═O, $R_3$ is $C_{2-9}$ alkyl, $R_4$ is H, then Y is not CHOH;

(7) $R_1$=$R_2$ is OH, W=CH═CH and X=C═O, $R_3$ is $C_9$ alkyl, $R_4$ is H, then Y is not CHOH ([10]-nordehydrogingerols);

(8) $R_1$=$R_2$ is OH, W=$CH_2CH_2$ and X=C═O, $R_3$ is $C_{2-12}$ alkyl, $R_4$ is H, then Y is not CHOH (norgingerols); and (9) $R_1$ is $OC_{1-4}$ alkyl or OH, $R_2$ is OH, W is $CH_2CH_2$, $R_3$ is $C_{2-12}$ alkyl, $R_4$ is H and X is CHOH, then Y is not CHOH (gingerdiols or norgingerdiols).

2. A method for inhibition of platelet aggregation in a subject in need of such inhibition comprising administering to said subject an amount effective to inhibit platelet aggregation of a compound of formula (I) or a pharmaceutically acceptable derivative thereof:

(I)

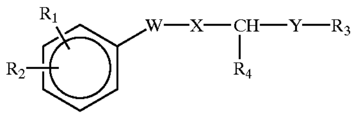

where $R_1$ is H, OH, $OC_{1-4}$alkyl, $NO_2$ $R_2$ is OH, $OC_{2-4}$alkyl, OC=$OC_{1-4}$alkyl or OC=OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR', where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2CO$, CH(OH)—$CH_2$, $C(CH_3)(OH)CH_2$, $CH_2CH(OH)$, $CH_2C(CH_3)OH$, CO, CHOH $C(CH_3)(OH)$, $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O; provided that one of W, X or Y has an OH group.

3. A pharmaceutical composition comprising a compound of claim 1 or a pharmaceutically acceptable derivative thereof and a pharmaceutically acceptable carrier.

4. A compound selected from the group consisting of:

1-(4-hydroxy-3-methoxyphenyl)dodecan-3-ol;
1-(4-hydroxy-3-methoxyphenyl)dodecan-5-ol;
3-methyl-1-(4-hydroxy-3-methoxyphenyl)undecan-3-ol;
3-methyl-1-(4-hydroxy-3-methoxyphenyl)tridecan-3-ol;
3-hydroxy-1-(4-hydroxy-3-methoxyphenyl)dodecan-5-one;
3-hydrox-y-1-(4-hydroxy-3-methoxyphenyl)decan-1-one;
3-hydroxy-1-(4-hydroxy-3-methoxyphenyl)dodecan-1-one;
1-hydroxy-1-(4-hydroxy-3-methox-yphenyl)undecan-2-one;
2-hydroxy-1-(4-hydroxy-3-methoxyphenyl)undecan-1-one;
5-hydroxy-1-(4-hydroxyphenyl)decan-3-one;
5-hydroxy-1-(4-hydroxyphenyl)dodecan-3-one;
5-hydroxy-1-(4-hydroxyphenyl)dodecan-1-ene-3-one;
5-hydroxy-1-(3,4-methylenedioxyphenyl)dodecan-3-one;
5,12-dihydroxy-1,16-bis(4-hydroxy-3-methoxyphenyl) hexadecane-3,14-dione;
1-(4-hydroxy-3-methoxyphenyl)dodecane-1,4-diene-3-one;
2-hydrox-y-1-(3,4-dimethoxy-phenyl)dodecan-3-one;
2-hydroxy-1-(3,4-dimethoxyphenyl)undecan-4-one; and
1-(3,4-dimethoxyphenyl)dodecan-2-ol.

5. A compound of claim 4 selected from the group consisting of:

1-(4-hydroxy-3 -methoxyphenyl)dodecan-3-ol;
3-hydroxy-1-(4-hydroxy-3-methoxyphenyl)dodecan-5-one;
3-hydroxy-1-(4-hydroxy-3-methoxyphenyl)decan-1-one; and
3-hydroxy-1-(4-hydroxy-3-methoxyphenyl)dodecan-1-one.

6. A method for treatment or prophylaxis of pain by action on sensory nerves or through anti-inflammatory action or through neurokinin inhibitory action in a subject in need of such treatment or prophylaxis comprising administering to said subject an effective amount of a compound of formula (I) or a pharmaceutically acceptable derivative thereof:

(I)

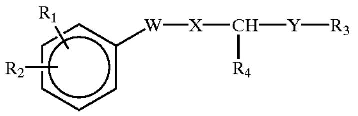

where $R_1$ is H, OH, $OC_{1-4}$alkyl, $NO_2$, $R_2$ is OH, $OC_{1-4}$alkyl, OC=$OC_{1-4}$alkyl or OC=OPh where the Ph can be optionally substituted by halogen, $C_{1-2}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, =O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, =O, nitro, halogen, —NRR', —COOR or —CONRR' where R and R' are H or $C_{1-4}$alkyl;

$R_4$ is H, $CH_3$, OH or =O; when $R_4$ is =O, then the carbon to which $R_4$ is attached is not bonded to H;

W is C(=O)—$CH_2$, CH=CH—, $CH_2O$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)OH$, $CH_2$, $CH(CH_3)$ or —C=O;

Y is —CH—OH, $C(CH_3)OH$, $CH_2$, $CH(CH_3)$ or —C=O; provided that one of W, X or Y has an OH group.

7. A method according to claim 6 wherein said compound or pharmaceutically acceptable derivative thereof is used as an analgesic.

8. A method for treatment or prophylaxis of cardiovascular disease in a subject in need of such treatment or prophylaxis comprising administering to said subject an effective amount of a compound of formula (I) or a pharmaceutically acceptable derivative thereof:

(I)

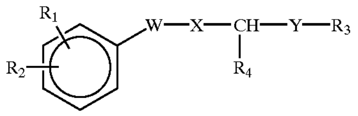

where $R_1$ is H, OH, $OC_{1-4}$alkyl, $NO_2$ $R_2$ is OH, $OC_{1-4}$alkyl, OC═$OC_{1-4}$alkyl or OC═OPh where the Ph can be optionally substituted by halogen, $C_{1-3}$ alkyl or $NO_2$;

$R_1$ and $R_2$ along with the two carbon atoms of the phenyl ring to which they are attached can combine to form a 5 or 6 membered heterocyclic ring comprising 1 or 2 heteroatoms selected from O, S or N;

$R_3$ is $C_{2-12}$alkyl, $C_{2-12}$alkenyl or $C_{2-12}$alkynyl each optionally substituted by one or more substituents selected from —OR, ═O, nitro, halogen, —NRR', —COOR or —CONRR' where R and R' are H or $C_{1-4}$alkyl;

$R_3$ may be a linking group of a bis compound where $R_3$ is $C_{2-12}$alkylene, $C_{2-12}$alkenylene or $C_{2-12}$alkynylene each optionally substituted by one or more substituents selected from —OR, ═O, nitro, halogen, —NRR', —COOR or —CONRR' where R and R' are H or $C_{2-4}$alkyl;

$R_4$ is H, $CH_3$, OH or =O; when $R_4$ is ═O, then the carbon to which $R_4$ is attached is not bonded to H;

W is C(═O)—$CH_2$, CH═CH—, $CH_2CO$, CH(OH)—$CH_2$, $C(CH_3)(OH)CH_2$, $CH_2CH(OH)$, $CH_2C(CH_3)OH$, CO, CHOH, $C(CH_3)(OH)$, $CH_2$, $CH_2CH_2$;

X is —CH—OH, $C(CH_3)OH$, $CH_2$, $CH(CH_3)$ or —C═O;

Y is —CH—OH, $C(CH_3)OH$, $CH_2$, $CH(CH_3)$ or —C═O;

provided that one of W, X or Y has an OH group.

9. A process of preparing a compound having a formula selected from the following group:

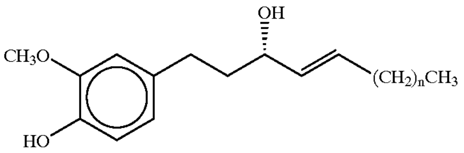

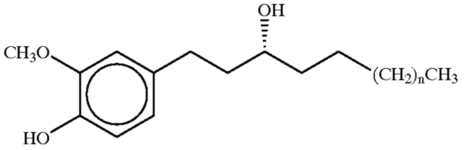

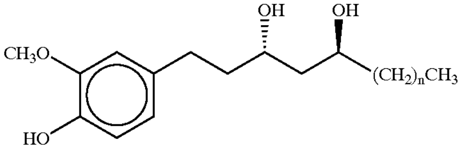

n=1–10 which method comprises treating ginger extract with heat or acid, followed by treating the extract with a microorganism or a microbial enzyme.

* * * * *

UNITED STATES PATENT AND TRADEMARK OFFICE
CERTIFICATE OF CORRECTION

PATENT NO. : 6,518,315 B1
DATED : February 11, 2003
INVENTOR(S) : Basil Don Roufogalis et al.

It is certified that error appears in the above-identified patent and that said Letters Patent is hereby corrected as shown below:

Title page, Item [54] and Column 1, line 1,
Title, "MEDICINAL USES OF PHENYLAIKANOLS AND DERIVATIVES" should read -- MEDICINAL USES OF PHENYLALKANOLS AND DERIVATIVES --.

Title page,
Item [57], ABSTRACT,
Line 9, "hydroycarby" should read -- hydrocarbyl --.
Item [56], References Cited, OTHER PUBLICATIONS,
"Denniff, P.," reference, "(+)-[n]-gingerols" should read -- (-)-[n]-gingerols --.
"Hikino, H.," reference, "ginerols" should read -- gingerols --.
"Takeda, S.," reference, "1-(4-hydroxy-3-methoxyphenyl)-4-decen-3-01" should read -- 1-(4-hydroxy-3-methoxyphenyl)-4-decen-3-ol --.
"Yamahara, J.," reference, "*officinale*Roscoe" should read -- *officinale* Roscoe --.
"Takahashi, N.," reference, "Niger." should read -- niger. --.

Column 11,
Line 13, "$CH_2CH2$" should read -- $CH_2CH_2$ --.
Line 14, "CH2" should read -- $CH_2$ --.
Line 48, "Where n = 0.4" should read -- Where n = 0 - 4 --.

Column 16,
Line 59, "Gincerol" should read -- Gingerol --.

Column 18,
Line 63, "arachlidonic" should read -- arachidonic --.

Column 22,
Line 21, "$^1$-NNR" should read -- $^1$H-NMR --.

Column 49,
Line 40, after "Tran, V H. Structure-activity relationship and" insert:
-- cardioactivity of phenolic substances acting on Ca2+ATPases. PhD Thesis, University of Sydney (1997).
Triggle, DJ. Cellular calcium metabolism: Activation and antagonism. J. Asthma (1984), 21, 376-385.
Vincenzi, FF. Calmodulin pharmacology. Cell Calcium (1981), 2, 387-409.
Turner, NJ. Asymmetric synthesis using enzymes and whole cells. In Advanced asymmetric synthesis. Edited by Stephenson, GR (1996), pages 260-274.
Wood J.N. (ed.), (1993) Capsaicin in the Study of Pain, Academic, New York, pp 268 --

UNITED STATES PATENT AND TRADEMARK OFFICE

CERTIFICATE OF CORRECTION

PATENT NO. : 6,518,315 B1
DATED : February 11, 2003
INVENTOR(S) : Basil Don Roufogalis et al.

It is certified that error appears in the above-identified patent and that said Letters Patent is hereby corrected as shown below:

Column 50,
Line 40, "$C(CH_3)$ OH" should read -- $C(CH_3)OH$ --.

Column 51,
Line 19, "$OC_{2-4}$alkyl," should read -- $OC_{1-4}$alkyl, --.
Line 41, "CHOH $C(CH_3)(OH)$" should read -- CHOH, $C(CH_3)(OH)$ --.

Column 52,
Line 9, "1-(4-hydroxy-3-methoxyphenyl)dodecan-3-ol" should read -- 1-(4-hydroxy-3-methoxyphenyl)dodecan-3-ol --.
Line 33, "$C_{1-2}$ alkyl" should read -- $C_{1-3}$alkyl --.
Line 52, "$CH_2O$" should read -- $CH_2CO$ --.

Column 53,
Line 29, "$C_{2-4}$ alkyl" should read -- $C_{1-4}$alkyl --.

Signed and Sealed this

First Day of March, 2005

JON W. DUDAS
*Director of the United States Patent and Trademark Office*